United States Patent
Biscup

(10) Patent No.: US 8,070,785 B2
(45) Date of Patent: Dec. 6, 2011

(54) BONE ANCHOR PROSTHESIS AND SYSTEM

(75) Inventor: Robert S. Biscup, Ft. Lauderdale, FL (US)

(73) Assignee: Spineco, Inc., Avon, OH (US)

( * ) Notice: Subject to any disclaimer, the term of this patent is extended or adjusted under 35 U.S.C. 154(b) by 1994 days.

(21) Appl. No.: 10/828,149

(22) Filed: Apr. 20, 2004

(65) Prior Publication Data
US 2005/0059972 A1    Mar. 17, 2005

Related U.S. Application Data

(60) Provisional application No. 60/502,957, filed on Sep. 16, 2003.

(51) Int. Cl.
*A61B 17/04* (2006.01)
*A61B 17/84* (2006.01)

(52) U.S. Cl. .................. 606/305; 606/306; 606/308

(58) Field of Classification Search ............ 606/72, 606/300–320; 408/199–203, 204, 214, 222, 408/239 R, 239 A; 403/1, 6–9, 11, 19, 204, 403/299–312, 341–343, 361, 362
See application file for complete search history.

(56) References Cited

U.S. PATENT DOCUMENTS

| | | | |
|---|---|---|---|
| 3,918,440 A * | 11/1975 | Kraus | ............... 602/2 |
| 4,027,392 A | 6/1977 | Sawyer et al. | |
| 4,306,564 A | 12/1981 | Kraus | |
| 4,351,337 A | 9/1982 | Sidman | |
| 4,359,318 A | 11/1982 | Gittleman | |
| 4,523,910 A | 6/1985 | Makovich | |
| 4,640,271 A * | 2/1987 | Lower | ............... 606/65 |
| 4,653,489 A | 3/1987 | Tronzo | |
| 4,701,180 A | 10/1987 | Kelly et al. | |
| 4,781,591 A | 11/1988 | Allen | |
| 4,877,019 A | 10/1989 | Vives | |
| 4,886,074 A | 12/1989 | Bisping | |
| 5,129,388 A | 7/1992 | Vignaud et al. | |
| 5,129,900 A | 7/1992 | Asher et al. | |
| 5,292,252 A | 3/1994 | Nickerson et al. | |
| 5,387,212 A | 2/1995 | Yuan et al. | |
| 5,562,670 A | 10/1996 | Brånemark | |
| 5,571,139 A | 11/1996 | Jenkins, Jr. | |
| 5,584,688 A | 12/1996 | Sakuma et al. | |

(Continued)

FOREIGN PATENT DOCUMENTS

DE    4107480    2/1992

(Continued)

*Primary Examiner* — Eduardo C Robert
*Assistant Examiner* — Tara Carter
(74) *Attorney, Agent, or Firm* — Fay Sharpe LLP; Brian E. Turung

(57) ABSTRACT

A prosthetic screw system that includes a prosthetic screw for at least partial insertion into a bone and/or cartilage. The prosthetic screw includes a head and a lower portion connected to the head. The prosthetic screw system also includes a set of head-pieces that can be connected to the head of the prosthetic screw. The head-pieces have differing configurations that are designed to be connected to different types of components of a prosthetic system. The universal connection arrangement between the prosthetic screw and the set of head-pieces enables the prosthetic screw to be customized for connection with a variety of components of a prosthetic system. The head-pieces can alternatively or additionally include a mechanical and/or electrical mechanism that provides one or more substances (e.g., medicine and/or other biological agent, etc.) and/or electrostimulation to a surgical site.

34 Claims, 9 Drawing Sheets

U.S. PATENT DOCUMENTS

| | | | | |
|---|---|---|---|---|
| 5,683,391 A | * | 11/1997 | Boyd | 606/61 |
| 5,725,377 A | | 3/1998 | Lemler et al. | |
| 5,836,935 A | | 11/1998 | Ashton et al. | |
| 5,871,484 A | | 2/1999 | Spievack et al. | |
| 5,882,350 A | | 3/1999 | Ralph et al. | |
| 5,968,098 A | | 10/1999 | Winslow | |
| 5,989,254 A | | 11/1999 | Katz | |
| 5,997,539 A | | 12/1999 | Errico et al. | |
| 6,004,322 A | | 12/1999 | Bernstein | |
| 6,005,349 A | | 12/1999 | Kunhardt et al. | |
| 6,017,344 A | | 1/2000 | Errico et al. | |
| 6,034,295 A | | 3/2000 | Rehberg et al. | |
| 6,053,917 A | | 4/2000 | Sherman et al. | |
| 6,056,753 A | | 5/2000 | Jackson | |
| 6,083,227 A | | 7/2000 | Saurat et al. | |
| 6,113,601 A | | 9/2000 | Tatar | |
| 6,120,502 A | * | 9/2000 | Michelson | 606/61 |
| 6,183,472 B1 | | 2/2001 | Lutz | |
| 6,224,596 B1 | | 5/2001 | Jackson | |
| 6,319,254 B1 | | 11/2001 | Giet et al. | |
| 6,340,588 B1 | | 1/2002 | Nova et al. | |
| 6,368,319 B1 | | 4/2002 | Schaefer | |
| 6,375,657 B1 | | 4/2002 | Doubler et al. | |
| 6,402,752 B2 | | 6/2002 | Schaffler-Wachter et al. | |
| 6,454,807 B1 | | 9/2002 | Jackson | |
| 6,511,481 B2 | | 1/2003 | Von Hoffmann et al. | |
| 6,554,830 B1 | | 4/2003 | Chappius | |
| 6,565,567 B1 | | 5/2003 | Haider | |
| 6,565,569 B1 | | 5/2003 | Assaker et al. | |
| 6,565,572 B2 | * | 5/2003 | Chappius | 606/73 |
| 6,654,629 B2 | | 11/2003 | Montegrande | |
| 6,669,697 B1 | * | 12/2003 | Pisharodi | 606/61 |
| 6,778,861 B1 | | 8/2004 | Liebrecht et al. | |
| 2001/0007074 A1 | * | 7/2001 | Strobel et al. | 606/73 |
| 2002/0029043 A1 | * | 3/2002 | Ahrens et al. | 606/73 |
| 2002/0049394 A1 | | 4/2002 | Roy et al. | |
| 2002/0095187 A1 | | 7/2002 | Thompson et al. | |
| 2002/0161367 A1 | | 10/2002 | Ferree | |
| 2004/0073221 A1 | * | 4/2004 | Biscup | 606/73 |
| 2004/0193166 A1 | * | 9/2004 | Biscup | 606/73 |
| 2004/0243130 A1 | * | 12/2004 | Biscup | 606/73 |
| 2005/0059972 A1 | | 3/2005 | Biscup | |
| 2006/0036253 A1 | | 2/2006 | Leroux | |

FOREIGN PATENT DOCUMENTS

| | | |
|---|---|---|
| EP | 0553 424 A1 | 8/1993 |
| WO | WO 02/076315 A1 | 10/2002 |

* cited by examiner

BONE ANCHOR PROSTHESIS AND SYSTEM

The present invention claims priority on U.S. Provisional Patent Application Ser. No. 60/502,957 filed Sep. 16, 2003 entitled "Bone Anchor Prosthesis and System", which is incorporated herein by reference.

The present invention pertains to prosthetic implants, and more particularly to bone screws, nails or posts that can be inserted into bone and/or cartilage, and more particularly to pedicle screws, nails or posts that can be inserted into a vertebra.

BACKGROUND OF THE INVENTION

The human spine is made up of a column of thirty-three bones and their adjoining structures. The bodies of these vertebrae are connected by anterior and posterior ligaments and by discs of fibrocartilage generally known as intervertebral discs. These discs are positioned between opposite faces of adjacent vertebral bodies. This column of vertebrae and intervertebral discs forms a central axis that supports the head and torso. These vertebrae also enclose an opening through which the spinal cord passes.

The presaccral vertebrae are normally held in position to one another by the intervertebral discs, ligaments and musculature of the body. These vertebrae move relative to adjacent vertebrae thus permitting the head to be turned relative the body and providing a wide range of flexibility to the spine.

One of the most costly health problems in society involves back pain and pathology of the spine. These problems can affect individuals of all ages and can result in great suffering to victims. Back pain can be caused by several factors such as congenital deformities, traumatic injuries, degenerative changes to the spine, and the like. Such changes can cause painful excessive motion, or collapse of a motion segment resulting in the contraction of the spinal canal and compression of the neural structures, causing debilitating pain, paralysis or both, which in turn can result in nerve root compression or spinal stenosis.

Nerve conduction disorders can also be associated with intervertebral discs or the vertebrae themselves. One such condition is herniation of the intervertebral disc, in which a small amount of tissue protrudes from the sides of the disc into the foramen to compress the spinal cord. A second common condition involves the development of small bone spurs, termed osteophytes, along the posterior surface of the vertebral body, again impinging on the spinal cord.

Upon identification of these abnormalities, surgery may be required to correct the problem. For those problems associated with the formation of osteophytes or herniations of the intervertebral disc, one such surgical procedure is intervertebral discectomy. In this procedure, the involved vertebrae are exposed and the intervertebral disc is removed, thus removing the offending tissue or providing access for the removal of the bone osteophytes. A second procedure, termed a spinal fusion, may then be required to fix the vertebrae together to prevent movement and maintain a space originally occupied by the intervertebral disc. Although this procedure may result in some minor loss and flexibility in the spine, due to the relatively large number of vertebrae, the minor loss of mobility is typically acceptable.

For the replacement of a vertebra of the human spinal column, for the distraction of the spinal column, for the stabilization of the vertebrae and likewise, it is known to apply pedicle screws. The pedicle screw is screwed into the pedicle of the vertebra and the head of the pedicle screw is connected to suitable provisions, for example to a stabilizing system, to distraction rods, etc. During the treatment of the spine, the pedicle screw is generally first rotated into the pedicle. Subsequently, the insertion of the rod is effected.

A standard pedicle screw assembly comprises a screw having an externally threaded stem having in turn a head provided with parts allowing it to be secured to one end of a distraction rod. Typically two such pedicle screws are inserted into respective vertebrae and are secured to a rod to distract and/or stabilize a spinal column after, for instance, a disk operation. One commonly used pedicle screw is disclosed in German Patent No. 4,107,480, which is incorporated herein by reference, and includes a head that has a pair of outwardly projecting parallel ridges with overhanging inner edges. A cap formed with a pair of complementary inwardly open slots fits with these ridges. The pedicle screw is threaded into the vertebrae, an end of the rod is fitted to its outer end, the cap is then slid transverse to the pedicle screw axis and parallel to the rod over the rod to capture it, and finally a cap screw threaded into the cap and tightened to press the rod down against the head of the pedicle screw and thereby fix the rod, cap, and screw together. Many other pedicle screw designs have been developed to simplify the insertion of the pedicle screw into the pedicle, and/or to reduce damage to the pedicle screw and/or the pedicle during surgery. Some of these pedicle screw, nail or post designs are disclosed in U.S. Pat. Nos. 3,918,440; 4,653,489; 4,877,019; 5,292,252; 5,562,670; 5,571,139; 5,882,350; 5,989,254; 5,997,539; 6,004,322; 6,004,349; 6,017,344; 6,053,917; 6,056,753; 6,083,227; 6,113,601; 6,183,472; 6,224,596; 6,319,254; 6,368,319; 6,375,657; 6,402,752; and 6,554,830; U.S. patent Publication No. 2001/0007074 published Jul. 5, 2001; and 2001/0053913 published Dec. 20, 2001; 2002/0029043 published Mar. 7, 2002; and the patents cited and disclosed in such patents. All these designs of pedicle screws, nails or posts and the disclosure associated with such pedicle screws, nails or posts are incorporated herein by reference.

After the pedicle screw is inserted in the pedicle, the bone around the pedicle screw must heal to properly secure the pedicle screw in the bone. Any infection that occurs around the pedicle screw can slow the healing process and/or damage the bone around the pedicle screw thereby weakening the connection between the bone and pedicle screw. Typically, a patient is given antibiotics for several days after the surgery to reduce the occurrence of infection about the pedicle screw. The patient may also receive electrical stimulation during surgery to promote the healing process of the bone about the pedicle screw. Both of these techniques have improved the post-operative success of the surgical procedure; however, improved success rates are still needed. Several pedicle screw designs that can be used to promote healing of the bone about the pedicle screw are disclosed in U.S. patent application Ser. No. 10/269,601 filed Oct. 11, 2002, which is incorporated herein by reference.

Once the pedicle screw is positioned in the bone and/or cartilage, the top position of the pedicle screw is commonly connected other components such as a rod, pin, ball, etc. so as to provide a pedicle structure used to correct a problem with the spine. Each component typically has a unique shape, thereby requiring the head of the pedicle screw to have a specific and corresponding shape to enable connection between the component and the pedicle screw. Examples of a few of the many shapes of the head of pedicle screws are illustrated in U.S. Pat. Nos. 6,669,697; 6,565,569; 6,565,567; 5,387,212; 5,129,900; 5,129,388; U.S. patent Publication No. 2002/0161367 published Oct. 31, 2002; European Patent Application Publication No. 0553424 published Aug. 4, 1993; and PCT Patent Application Publication No. WO 02/076315 published Oct. 3, 2002, all of which are incorporated herein by reference. When a pedicle structure is being inserted during surgery, the proper type of pedicle screw must be inserted and oriented in a precise manner, or the pedicle structure will not fit properly together. During surgery, it is not uncommon for a pedicle screw to be inserted into bone or cartilage and later have to be removed because the pedicle screw can be used with the particular pedicle structure being built. The removal and reinsertion of another type of pedicle screw can result in increase surgery times, potential damage to the bone and/or cartilage and/or other complications.

In view of the present state of technology related to prosthetic implants, there is a continued need for pedicle screws that reduce the occurrence of post-operative failure, and which can be easily adapted for use with various types of components used to form pedicle structures.

SUMMARY OF THE INVENTION

The present invention pertains to an improved implant, and more particularly to an improved connector such as, but not limited to, a screw, nail or post which can be easily adapted for use with a variety of different components of a pedicle structure and/or be used with mechanical and/or electrical mechanism to provide biological substances and/or electrostimulation to a particular site. Although the present invention will be described with particular reference to screws, nails or posts for use in a vertebra and a method for use of such screws, nails or posts, the invention has much broader applications and pertains to a screw, nail or post that can be used in many other areas of a body and in many other types of bones.

In accordance with the principal feature of the present invention, there is provided an improved screw, nail or post used for insertion into bone and/or cartilage. The screw, nail or post is generally used to anchor and/or affix a support structure (e.g., rod, cage, stabilization system, etc.) to the bone and/or cartilage. As can be appreciated, the screw, nail or post can also be used for other uses such as, but not limited to, attachment of ligaments; connecting and/or repairing broken bones; reducing pain; stabilizing a tissue ligament, cartilage, and/or bone; an adjunct for another surgical procedure and the like. In one embodiment of the present invention, the screw, nail or post is used to repair a spinal column. During the replacement of a vertebra of the human and/or animal spinal column, the distraction of the spinal column, and/or the stabilization of the spinal column, pedicle screws, nails, and/or posts of the present invention can be used. Generally, the screw, nail, and/or post are inserted into the pedicle of the vertebra; however, the screw, nail or post can be connected to other regions of the vertebra. In still another and/or alternative embodiment of the invention, the screw, nail or post is used in areas of a body other than the spine. Such bones in such other areas include, but are not limited to, acromion, atlas, axis, calcaneus, carpus, clavicle, coccyx, epicondyle, epitrochlea, femur, fibula, frontal bone, greater trochanter, humerus, ilium, ischium, mandible, maxilla, metacarpus, metatarsus, occipital bone, olecranon, parietal bone, patella, phalanx, radius, ribs, sacrum, scapula, sternum, talus, tarsus, temporal bone, tibia, ulna, and/or zygomatic bone. In one aspect of the embodiment, the screw, nail or post is used to connect together fractured or broken bones. The bone or bones are not limited to bones of the vertebra, but include any bone in which the screw, nail or post can be used to at least partially heal the bone. In another and/or alternative aspect of the embodiment, the screw, nail or post is used to connect ligaments together and/or to bone and/or cartilage. In still another and/or alternative aspect of the embodiment, the screw, nail or post is used to retain tissue (e.g., organs, muscle, etc.) in place. In yet another and/or alternative embodiment of the present invention, the screw, nail or post includes a head and a lower portion. In one aspect of this embodiment, the top surface of the head can have a number of different shapes (e.g., flat, sloped, acuate, circular, polygonal, etc.). In another and/or alternative aspect of this embodiment, the head can have a number of different surfaces (e.g., smooth, rough, ribbed, etc.). In still another and/or alternative aspect of this embodiment, the head can have a number of different shapes (e.g., spherical, ellipsoidal, cubic, orthogonic, etc.). In yet another and/or alternative aspect of this embodiment, the head can have various side surfaces (e.g., ribs, grooves, slots, pits, etc.). In still yet another and/or alternative aspect of this embodiment, the head can include one or more openings and/or channels designed to at least partially secure one or more components to the head. In still another and/or alternative aspect of this embodiment, the head can include one or more connectors designed to at least partially secure one or more components to the head. In a further and/or alternative aspect of this embodiment, the head can be rigidly connected to the lower portion, moveably connected to the lower portion, or removably connected to the lower portion. The shapes, surfaces, connectors, and/or openings of the head, and/or the type of connection between the head and lower portion i) facilitate in the insertion and/or removal of the screw, nail or post into bone and/or cartilage, ii) facilitate in the attachment and/or disconnection of the head from other components (e.g., a stabilizing system, distraction rods, cage, nuts, bolts, mechanical and/or electrical mechanisms, insertion and/or removal tools, etc.), and/or iii) facilitate in the operation of the implant and/or components connected to the screw, nail or post. In a further and/or alternative embodiment of the invention, the head can be made from one or more materials. The shape, materials, outer surface features, internal features of the head can be selected to obtain the desired rigidity, flexibility, strength, hardness, etc. of the head. In another and/or alternative embodiment of the invention, the lower portion of the screw includes a threaded outer surface. The nail or post may or may not have a threaded surface. In still another and/or alternative embodiment of the invention, the lower portion of the screw, nail or post can have a smooth surface, ribs, channels, spikes or barbs, threads, teeth, etc. In yet another and/or alternative embodiment of the invention, the end of the lower portion of the screw, nail or post can be flat, sharp, forked, etc. In still yet another and/or alternative embodiment of the invention, the cross-sectional shape and/or area along the length of the lower portion can be constant or can vary. In one aspect of this embodiment, the cross-sectional shape and/or area along the length of the lower portion remains substantially constant. In another and/or alternative aspect of this embodiment, the cross-sectional shape and/or area along the length of the lower portion tapers along at least a portion of the lower portion. In a further and/or alternative embodiment of the invention, the lower portion can have a number of cross-sectional shapes (e.g., circular, polygonal, oval, arcuate, etc.). In a still further and/or alternative embodiment of the invention, the lower portion can be made from one or more materials. The shape, materials, outer surface features, and/or internal features of the lower portion can be selected to obtain the desired rigidity, flexibility, strength, hardness, etc. of the lower portion. In still another and/or alternative embodiment of the present invention, at least a portion of the head of the screw, nail or post can be designed to break off after inserting the lower portion into the bone and/or cartilage, and/or after the connection of one or more components to the screw, nail or post. In still yet another and/or alternative embodiment of the present invention, a lower portion of the screw, nail or post can include a feature (e.g., bore, notch, etc.) which facilitates subsequent removal of the lower portion from the location in which it is secured, and/or facilitate in the connection of one or more components and/or devices to the lower portion. In a further and/or alternative embodiment of the present invention, the lower portion can lie in a single axis or multiple axes. In one aspect of this embodiment, the one or more axes of the lower portion are fixed. In another and/or alternative aspect of this embodiment, the one or more axes of the lower portion can be altered. In essence, the screw, nail, or post has a configuration that suits the particular application of the screw, nail or post. In still further and/or alternative embodiment of the present invention, the screw, nail or post is designed to firmly secure one or more components (e.g., a stabilizing system, distraction rods, cage, nuts, bolts, mechanical and/or electrical mechanisms, insertion and/or removal tools, etc.) to bone and/or cartilage to thereby reduce or prevent rotational or translational movement of one or more components of the implant. In yet a further and/or alternative embodiment of the present invention, the screw, nail or post is designed to be relatively small yet constructed to withstand sufficiently high torque and/or compressive forces to firmly set the screw, nail or post in the bone and/or cartilage. In still yet a further and/or alternative embodiment of the present invention, the screw, nail or post is designed to be easily manipulated to permit relatively rapid insertion and/or tightening during surgical procedures.

In another and/or alternative aspect of the invention, the screw, nail or post has a head wherein the head includes a male-extension member and/or a female internal chamber. The male-extension member and/or a female internal chamber are designed to allow a common family of attachments (herein called "head-pieces") to be attached onto or into the head of the screw, nail or post. These head-pieces are used to connect and/or be used with one or more components of a support system (e.g., a stabilizing system, distraction rods, cage, nuts, bolts, mechanical and/or electrical mechanisms, insertion and/or removal tools, etc.). The head-pieces can have a variety of shapes and sizes so as to enable the head of the screw, nail or post to be connected to a variety of different components of a support system. The head-pieces can be designed in a variety of shapes, sizes and/or configurations to meet specific surgical needs. Some non-limiting examples of the head-piece design include, but are not limited to, a connection tower with an exterior threaded shaft, a closed-rod connector, an open rod connector, a cross connector, a universal polyaxial connector, a spinal plate connector, a wire fixation device, an artificial ligament "facet", etc. As such, the head-pieces can be used to i) attach and/or be connected to spinal plates, ii) attach and/or be connected to one or more rods that are connected to another vertebra, iii) attach and/or be connected to one or more rods that are connected to one or more devices which in turn are connected to one or more vertebra, iv) attach and/or be connected to one or more rods that extend to or are connected to other regions of a body, v) attach and/or be connected to one or more wire fixation devices, vi) attach and/or be connected to a universal polyaxial connector, vii) attach and/or connect together two or more rods, plates, and/or other medical devices, viii) attach and/or be connected to ligaments (natural and/or artificial, etc.), ix) attach and/or be connected to other types of tissue, x) attach and/or be connected to various types of medical hardware (e.g., pulley, pivoting mechanisms, pump, electrical device, davits, prosthetic devices, etc.), etc. As can be appreciated, other uses can be contemplated for the head-piece. The head-piece can be designed to remain substantially stationary relative to the screw, nail or post, at least partially rotate or swivel relative to the screw, nail or post, and/or at least partially pivot relative to the screw, nail or post. The particular head-piece selected will in part depend on the specific needs for the device. The connectability of the head-piece enables a selected head-piece to changed out with another if it is determined prior to and/or during the course of a medical procedure and a different head-piece should be used to better accomplish the desired medical procedure. As such a series or family of head-pieces can be manufactured for use with a corresponding family of screws, nails or posts. For instance a Series A screw, nail or post could be a screw, nail or post having a certain sized and shaped male extension member to be used with complementary Type A head-pieces. The Series A screws, nails or posts could have different lengths, sizes and/or shapes of the head and/or lower portion of the screw, nail or post so that the screw, nail or post can be properly inserted in various bones and/or cartilages in a body; however, each of these screws, nails or posts would have the same sized and shaped male extension member so that any Type A head-piece could be connected to the screw, nail or post. In another non-limiting example, a Series B screw, nail or post could be a screw, nail or post having a certain sized and shaped female internal chamber to be used with complementary Type B head-pieces. The Series B screws, nails or posts could have different lengths, sizes and/or shapes of the head and/or lower portion of the screw, nail or post so that the screw, nail or post can be properly inserted in various bones and/or cartilages in a body; however, each of these screws, nails or posts would have the same sized and shaped female internal chamber so that any Type B head-piece could be connected to the screw, nail or post. In one specific example, each of the head-pieces that belong to a particular family or type includes a marking to indicate that family or type of head-piece that can be used with a particular screw, nail or post. As can be appreciated, the screw, nail or post can also include a marking to identify the family or type of head-piece that can be connected to the screw or post. Many types of markings can be used including, but not limited to, a number code, a letter code, a symbol code, a color code or combinations thereof. When the head of the screw, nail or post includes a male extension member, the male extension member can be a shaft and/or other structure extending from the head (e.g., top, edges, side, etc.). The male extension member can at least partially include one or more threads, ribs, slots, notches, grooves, channels, cavities, openings, etc. The male extension member can have a uniform or varied cross-sectional area along the longitudinal axis of the extension. The male extension member can have a constant or a number of different cross-sectional shapes (e.g., circular, oval, polygonal, curvilinear, etc.) along the longitudinal axis of the extension. When the head of the screw, nail or post includes a female internal chamber, the female internal chamber can be located on a variety of different regions on the head (e.g., top, edges, side, etc.). The female internal chamber can at least partially include one or more threads, ribs, slots, notches, channels, side openings, cavities grooves, etc. The female internal chamber can have a uniform or varied cross-sectional area along the longitudinal axis of the chamber. The female internal chamber can have a constant or a number of different cross-sectional shapes (e.g., circular, oval, polygonal, curvilinear, etc.) along the longitudinal axis of the chamber. The male extension member or female internal chamber on the head of the screw, nail or post can include one or more shapes or arrangements that are designed to permanently or semi-permanently lock and secure one or more of the head-pieces to the screw, nail or post. In one embodiment of the invention, the head-piece includes an anchor end that is designed to be secured to a female internal chamber in the head of a screw, nail or post. In one non-limiting aspect of this embodiment, the anchor end includes one or more threads, ribs, slots, etc. so as to be threaded and/or otherwise secured in a female internal chamber of the head of the screw, nail or post. The anchor end can be tapered or non-tapered. In another and/or non-limiting aspect of this embodiment, the anchor end in insertable into a female internal chamber of the head of the screw, nail or post and is thereafter secured and/or locked to the head of the screw, nail or post by one or more mechanism (e.g., screw, wedge, adhesive, clamp, etc.). In another and/or alternative embodiment of the invention, the head-piece includes a connection cavity that is designed to be secured to a male extension member on the head of the screw, nail or post. In one non-limiting aspect of this embodiment, the male extension member includes one or more threads, ribs, slots, etc. so as to be threaded into a connection cavity of the head-piece. The male extension member can be tapered or non-tapered. In another and/or non-limiting aspect of this embodiment, the male extension member is insertable into the connection cavity of the head-piece and is thereafter secured and/or locked to the head-piece by one or more mechanism (e.g., screw, wedge, adhesive, clamp, etc.). In still another and/or alternative embodiment of the invention, the male extension member or female internal chamber of the head of the screw, nail or post is permanently or semi-permanently locked and/or secured one or more of the head-pieces. The locking or securing arrangement can include, but is not limited to, gripping inserts, expanding locking inserts, etc. In still another and/or alternative embodiment of the invention, the female internal chamber of the head of the screw, nail or post and/or the connection cavity of the head-pieces includes a secondary channel beginning at or closely adjacent to the base of the female internal chamber or connection cavity. The secondary channel is designed to accept and connect to a male extension member or anchor end that is smaller in cross-sectional shape than the cross-sectional shape of the female internal chamber or connection cavity. As such, the secondary connection cavity enables a head-piece having an anchor which is too small to connect to the female internal chamber of a screw, nail or post to be secured to the secondary connection cavity so that the head-piece can be used with the screw, nail or post. In addition, the secondary connection cavity enables a male extension member of a head of a screw, nail or post which is too small to connect to the connection cavity of a head-piece to be secured to the secondary connection cavity so that the head-piece can be used with the screw, nail or post. In yet another and/or alternative embodiment of the invention, the end region of the anchor of a head-piece includes a forked or split end and the anchor includes one or more internal chambers. The one or more channels are designed to receive a wedge or driver that causes the fork or split in the end region of the anchor to expand as the wedge or driver inserted into the one or more channels. A threaded arrangement or other arrangement can be used to facilitate inserting and/or maintaining the wedge or driver into one or more channels. The wedge or driver can be torqued into the one or more channels, hammered into one or more channels, hydraulically inserted into one or more channels, etc. The expansion of the fork or split facilitates in the securing of the head-piece in the female internal chamber in the head of the screw, nail or post. Additionally or alternatively, the wedge or driver could act upon or more components in the screw, nail or post to cause one or more regions in the lower portion of the screw, nail or post to expand and/or buckle out to thereby facilitating in securing the lower portion in the bone and/or cartilage. The wedge or driver can be designed to be permanently secured into the one or more channels of the anchor or be designed so that it can be removed after performing its desired function.

In another and/or alternative aspect of the invention, the screw, nail or post, and/or head-piece includes one or more cavities or channels. The one or more cavities can be used for a variety of reasons such as, but not limited to, 1) weight distribution of the screw, nail or post and/or head-piece; 2) structural integrity of the screw, nail or post and/or head-piece (e.g., break points, flex points, compression points, etc.); 3) at least partially containing a substance such as, but not limited to, a material that a) promotes and/or inhibits bone and/or other tissue growth, b) inhibits rejection of the screw, nail or post and/or head-piece, c) inhibits rejection of components connected to and/or located adjacent to the screw, nail or post and/or head-piece, d) reduces infection, e) reduces inflammation, f) reduces pain, g) provides vitamins and/or minerals, h) provides genetic material, i) provides tissue, j) promotes healing of surrounding tissue, k) combats or cures cancer and/or other diseases, l) functions as a location and/or visual indicator, m) functions as a filler material, n) functions as an adhesive, and/or the like; and/or 4) at least partially contains one or more electrical and/or mechanical components. In one embodiment of the present invention, the screw, nail or post and/or head-piece includes a single cavity. In another and/or alterative embodiment of the present invention, the screw, nail or post and/or head-piece includes a plurality of cavities. In one aspect of this embodiment, at least one cavity is separated from one other cavity. The material in the cavity can be directly contained in the cavity or be at least partially contained within a bladder or bag at least partially positioned in the cavity. The screw, nail or post that includes one or more cavities containing a material can be designed to enable the material to at least partially naturally leach out, seep out, flow out, etc. of the screw, nail or post and/or be design to at least partially cause the material to exit the screw, nail or post by use of one or more mechanical and/or electrical devices. In another and/or alternative aspect of this embodiment, two or more cavities are connected together by one or more passageways. In still another and/or alternative embodiment of the present invention, at least one cavity has at least one access opening to the surface of the screw, nail or post and/or head-piece. The access opening is generally designed to allow fluids and/or other material to flow into and/or out of the cavity. The size of the access is generally sized to regulate or control the fluid and/or material flow through the access opening (e.g., to control the time release of material from the nail, screw or post via gravity and/or some other mechanism). In yet another and/or alternative embodiment of the invention, the size of the one or more cavities is less than about 70% of the total volume of the screw, nail or post and/or head-piece. In one aspect of this embodiment, the size of the one or more cavities is generally less than about 50% of the total volume of the screw, nail or post and/or head-piece, typically less than about 40% of the total volume of the screw, nail or post and/or head-piece, more typically less than about 30% of the total volume of the screw, nail or post and/or head-piece, still more typically less than about 20% of the total volume of the screw, nail or post and/or head-piece, and even more typically less than about 10% of the total volume of the screw, nail or post and/or head-piece. In still yet another and/or alternative embodiment of the present invention, the shape of the one or more cavities is selected for a particular application of the one or more cavities. Any number of cavity shapes can be used (e.g., spherical, cylindrical, ovoid, pyramidal, cubical, orthogonic, etc.). Two or more cavities can have the same or different shape and/or volume. In a further and/or alternative embodiment of the present invention, the one or more cavities are located in the head of the screw, nail or post. In one aspect of this embodiment, at least a majority of the cavities and/or the majority of the volume of the cavities are located in the head. In still a further and/or alternative embodiment of the present invention, the one or more cavities are located in the lower portion of the screw, nail or post. In one aspect of this embodiment, at least a majority of the cavities and/or a majority of the volume of the cavities are located in the lower portion. In another and/or alternative aspect of this embodiment, the same number of cavities and/or the same volume of the cavities is located in the head and lower portion. In still yet a further and/or alternative embodiment of the present invention, the one or more cavities are located in the head-piece.

In still another and/or alternative aspect of the present invention, one or more substances are included on and/or in the screw, nail or post and/or head-piece to improve the success of inserting the screw, nail, or post into the bone and/or cartilage; to improve the success of inserting the head-piece on the screw, nail or post; to reduce rejection of and/or infection associated with the screw, nail or post, the head-piece and/or the support system; and/or to promote healing about the screw, nail or post, the head-piece and/or support system. In one embodiment of the present invention, the substance includes, but is not limited to, antithrombogenic agents; steroids; thioprotese inhibitors; antimicrobials; antibiotics; tissue plasma activators; monoclonal antibodies; antifibrosis compounds; hormones; growth factors; anti-mitotic agents; immunosuppressive agents; sense or antisense oligonucleotides; nucleic acid analogues; inhibitors of transcription factor activity; anti-neoplastic compounds; chemotherapeutic compounds; radioactive agents; growth factors; antiplatlet compounds; antitabolite compounds; anti-inflammatory compounds; anticoagulent compounds; antimitotic compounds; antioxidants; antimetabolite compounds; anti-migratory agents; anti-matrix compounds; anti-vital compounds; anti-proliferatives; anti-fungal compounds; anti-protozoal compounds; human tissue; animal tissue; synthetic tissue; human cells, animal cells; synthetic cells; and/or bone-stimulation, bone-growth and/or bone-activating matter. In another and/or alternative embodiment of the present invention, one or more substances are included in one or more cavities of the screw, nail or post. In one aspect of this embodiment, one or more cavities includes a single type of substance. In still another and/or alternative embodiment of the present invention, the cavity includes multiple types of substances. In yet another and/or alternative embodiment of the present invention, one or more cavities can be partially or fully filled with one or more substances. In still yet another and/or alternative embodiment of the present invention, the one or more substances are partially or fully coated on the surface of the screw, nail or post, head-piece and/or support system.

In yet another and/or alternative aspect of the present invention, the one or more access openings in the surface of the screw, nail or post and/or head-piece allows for the insertion of one or more substances into one or more cavities of the screw, nail or post and/or head-piece; allows one or more substances to exit the one or more cavities of the screw, nail or post and/or head-piece; and/or to allow body fluids and/or bone growth into the one or more access openings and/or into the one or more cavities. In one embodiment of the present invention, a plurality of cavities includes at least one access opening. In another and/or alternative embodiment of the present invention, at least one access opening can be used by the manufacturer and/or physician to insert one or more substances into one or more cavities. As can be appreciated, a physician can add a substance into the cavity just prior to, during, and/or after the insertion of the screw, nail, or post in the bone and/or cartilage; during and/or after the connection of the head-piece to the screw, nail or post; and/or during and/or after the forming of the support system in the body. As can further be appreciated, a physician can add a substance into the cavity after the surgery has been completed and the patient is recovering from the surgery. In such a situation, the cavity can be periodically replenished with the same or different substance to facilitate in the recovery of the patient. In still another and/or alternative embodiment, the size of one or more of the access openings is selected to control or regulate the flow of substances into and/or out of the one or more access openings.

In still yet another and/or alternative aspect of the present invention, a cap and/or cover is applied over one or more access openings in the screw, nail or post and/or the head-piece. The cap or cover is designed to at least partially seal one or more substances in the one or more cavities and/or access openings, and/or to at least partially control the release of one or more substances from the one or more cavities. In one embodiment of the invention, the cap or cover is being made of a biodegradable and/or non-biodegradable material. In one aspect of this embodiment, the cap and/or cover is at least partially made of a biodegradable material which at least partially dissolves after the screw, nail or post has been implanted thereby at least partially providing access to the access opening over time. In another and/or alternative embodiment of the invention, the cap and/or cover can be inserted a) prior to, during, and/or after the insertion of the screw, nail, or post in the bone and/or cartilage, b) prior to, during, and/or after the insertion of the head-piece on the screw, nail, or post, and/or c) prior to, during, and/or after the assembly of the pedicle system. In still another and/or alternative embodiment of the invention, the cap and/or cover can be designed to be at least partially removed a) prior to, during, and/or after the insertion of the screw, nail, or post in the bone and/or cartilage, b) prior to, during, and/or after the insertion of the head-piece on the screw, nail, or post, and/or c) prior to, during, and/or after the assembly of the pedicle system. In yet another and/or alternative embodiment of the invention, the cap and/or cover is at least partially made of a material that allows one of more substances and/or body fluids to penetrate the cap or cover. In still yet another and/or alternative embodiment of the present invention, the cap and/or cover material includes, but is not limited to, metals, wood, fabric, carbon and/or glass fibers, polymers; copolymers; human tissue; animal tissue; synthetic tissue; human cells; animal cells; synthetic cells; and/or bone-stimulation, bone-growth and/or bone activating matter. In a further and/or alternative embodiment of the present invention, the cap and/or cover can be applied to the screw, nail or post and/or head-piece is a number of ways (e.g., dipping, spraying, ionizing, painting, adhesive, screwing, snapping, locking, tacking, soldering, melting, etc.).

In a further and/or alternative aspect of the invention, the screw, nail or post; head-piece and/or support system include one or more outer surface regions that are coated with one or more substances. In one embodiment of the present invention, the one or more substances include, but are not limited to, a substance that a) promotes and/or inhibits bone and/or other tissue growth, b) inhibits rejection of the screw, nail or post, c) inhibits rejection of components connected to and/or located adjacent to the screw, nail or post (e.g., head-piece, pedicle system (e.g., a stabilizing system, distraction rods, cage, nuts, bolts, mechanical and/or electrical mechanisms, insertion and/or removal tools, etc.), etc.), d) reduces infection, e)

reduces inflammation, f) reduces pain, g) provides vitamins, minerals, and/or nutrients, h) provides genetic material, i) provides tissue, j) facilitates in the insertion, positioning, and/or removal of the screw, nail or post from bone and/or cartilage (e.g., lubricant, Teflon, graphite, etc.), k) secures the screw, nail or post in the bone and/or cartilage (e.g., bone cement or other adhesive, etc.), l) promotes healing of surrounding tissue, m) combats cancer and/or other diseases, n) combats and/or cures biological abnormalities (e.g., a chemical imbalance, etc.), o) functions as a location and/or visual indicator, p) secures the head-pieces to the nail, screw or post (e.g., bone cement or other adhesive, etc.), q) facilitates in the insertion, positioning, and/or removal of the head-pieces from the screw, nail or post (e.g., lubricant, Teflon, graphite, etc.), and/or the like. Typically, the one or more coated substances are selected to improve the success of retaining the screw, nail, or post into the bone and/or cartilage; the rejection of the screw, nail or post, the headpiece and/or the support system after insertion in a body; and/or infection from the insertion of the screw, nail or post, the headpiece and/or the support system after insertion in a body. In another and/or alternative embodiment of the present invention, the coating includes a single type of substance. In still another and/or alternative embodiment of the present invention, the coating includes multiple types of substances. In another and/or alternative embodiment of the present invention, the surface of the screw, nail or post; head-piece; and/or support system that include the one or more substances are smooth, rough (e.g., ribs, canals, pits, teeth, ridges, grooves, holes, notches, slits, slots, channels, corrugations etc.), porous and/or non-porous. In yet another and/or alternative embodiment of the present invention, the coating is smooth and/or rough. In still yet another and/or alternative embodiment of the present invention, the coating includes a compound that at least partially controls the release of the one or more substances from the coating. The compound can be biodegradable or non-biodegradable. In still yet another and/or alternative embodiment of the present invention, the coating facilitates the insertion and/or securing of the screw, nail or post into bone and/or cartilage; the insertion and/or securing of head-piece in the screw, nail or post; and/or insertion and/or securing of the support system on the head-piece. In one aspect of this embodiment, the coating is a biocompatible material. In another and/or alternative aspect of this embodiment, the coating includes polytetrafluoroethylene, or polymers and/or copolymers that include polytetrafluoroethylene, a natural and/or synthetic bone cement; polymer, copolymer and/or urethane foam; autologous growth compound; powdered bone, bone and/or other tissue growth stimulating substances; polyglycolate polymers and/or analogues; lactides; polydioxamone; polyglycolate; lactide/glycolide copolymers; and/or other tissue growth inhibiting compounds; and/or other substances (e.g., antithrombogenic agents; steroids; thioprotese inhibitors; antimicrobials; antibiotics; tissue plasma activators; monoclonal antibodies; anti fibrosis compounds; hormones; growth factors; anti-mitotic agents; immunosuppressive agents; sense or antisense oligonucleotides; nucleic acid analogues; inhibitors of transcription factor activity; anti-neoplastic compounds; chemotherapeutic compounds; radioactive agents; growth factors; antiplatlet compounds; antitabolite compounds; anti-inflammatory compounds; anticoagulent compounds; antimitotic compounds; antioxidants; antimetabolite compounds; anti-migratory agents; anti-matrix compounds; anti-vital compounds; anti-proliferatives; anti-fungal compounds; anti-protozoal compounds; human tissue; animal tissue; synthetic tissue; human cells; animal cells; synthetic cells; and/or bone-stimulation, bone-growth and/or bone activating matter; etc.). In a further embodiment of the present invention, the coated material can be applied to the screw, nail or post, the head-piece and/or support system by adhesive bonding, welding, soldering, shrink wrapping, melting, spray coating, ionization, hot dipping, electroplating, immersion coating, brush coating, and/or the like. In another embodiment, the coating material enhances the strength and/or durability of the screw, nail or post, head-piece, and/or pedicle system; and/or hardens or softens the surface of the screw, nail or post, head-piece and/or support system. In still and/or alternative embodiment of the present invention, the one or more coatings of one or more substances are partially or fully coated on the surface of the screw, nail or post, head-piece and/or support system.

In another and/or alternative aspect of this invention, the screw, nail or post, and/or head-piece include at least one opening or mounting member used to connect and/or secure a) one or more devices to anchor and/or affix one or more components of the pedicle system (e.g., stabilizing system, distraction rods, cage, nuts, bolts, mechanical and/or electrical mechanisms, insertion and/or removal tools, etc.), and/or b) one or more components of the screw, nail or post, and/or head-piece (e.g., connect head to lower portion of screw, nail or post; connect head-piece to head and/or lower portion of screw, nail or post; connect an electrical and/or electronic component to the screw, nail or post; connect a mechanical component to the screw, nail or post; etc.). The one or more openings can be, but are not limited to, an access opening as described above, or some other opening. The one or more mounting members can be, but are not limited to, a ridge, groove, slot, etc. The one or more openings or mounting members can, but are not limited to, being positioned on the head and/or lower portion of the screw, nail or post, and/or head-piece.

In still another and/or alternative aspect of the invention, the screw, nail or post, and/or head-piece is made of a biodegradable and/or non-biodegradable material. In one embodiment of the invention, the screw, nail or post, and/or head-piece is at least partially made of a biodegradable material which at least partially dissolves or is absorbed after the screw, nail or post, and/or head-piece has been inserted in bone and/or cartilage. In one aspect of this embodiment, only a portion of the screw, nail or post, and/or head-piece is made of a biodegradable material. In another and/or alternative aspect of this embodiment, the biodegradable material forming at least a portion of the screw, nail or post, and/or head-piece is coated and/or selected of a material that biodegrades and/or is absorbed over a desired or predetermined period of time and/or at a desired or predetermined rate. In another and/or alternative aspect of this embodiment, the screw, nail or post, and/or head-piece is made of or includes a non-biodegradable material.

In still yet another and/or alternative aspect of the invention, there is provided a special set of tooling to a) facilitate in the insertion and/or removal of the head-piece into the screw, nail or post; b) facilitate in the insertion and/or removal of the screw, nail or post from bone and/or cartilage; c) facilitate in the locking and/or unlocking of the head-piece to the screw, nail or post (e.g., expansion of the anchor of the head-piece, etc.); d) facilitate in the insertion and/or removal of the lower portion on or from the head of the screw, nail or post, and/or e) facilitate in the insertion and/or removal of a mechanical and/or electrical mechanism from the screw, nail or post, and/or head-piece.

In yet another and/or alternative aspect of the invention, the screw, nail or post, and/or head-piece includes one or more mechanical and/or electrical devices that at least partially cause and/or control the release of one or more substances from the screw, nail or post, and/head-piece. In one embodiment of the present invention, the mechanical and/or electrical device can be designed to cause and/or control the release of one or more substances based upon, but not limited to, a) a preprogrammed schedule, b) a function of time, c) a predetermined rate, d) and/or receipt of an external signal. In one aspect of this embodiment, the mechanical and/or electrical device is preprogrammed to allow and/or cause the release one or more substances from the screw, nail or post, and/or head-piece during one or more time periods. In one non-limiting design, the mechanical and/or electrical device includes a microchip that at least partially stores a program that allows and/or causes the release one or more substances from the screw, nail or post, and/or head-piece. In one particular design, the mechanical and/or electrical device includes one or more MEMS (micro-electro-mechanical systems). The MEMS include both the preprogramming and the mechanism to allow and/or cause the release one or more substances from the screw, nail or post, and/or head-piece. In another and/or alternative particular design, the microchip at least partially controls a separate mechanical and/or electrical device (e.g., valve, pump, motor, etc.) which in turn allows and/or causes the release one or more substances from the screw, nail or post, and/or head-piece. In still another and/or alternative particular design, the microchip can be preprogrammed and/or reprogrammed prior to, during and/or after the insertion of the screw, nail or post, and/or head-piece. As can be appreciated, the parameters for allowing and/or causing the release of one or more substances can be altered by reprogramming (e.g., new data, additional data, new source code, additional source code, etc.) during the healing process of a patient, thus are individualized for a patient. Consequently, the setting for the mechanical and/or electrical device can be changed, as medical treatment needs dictate (e.g., greater or lesser amounts of substance discharge, different substance discharge ratios, more frequent substance discharge, etc.). In yet another and/or alternative particular design, the microchip can be activated prior to, during and/or after the insertion of the screw, nail or post, and/or head-piece. In another and/or alternative aspect of this embodiment, the external signal includes, but is not limited to, an electrical signal, a magnetic signal, an electromagnetic wave signal (e.g., light, radio wave, microwave, x-ray, infrared light, ultraviolet light, etc.), a heat signal, a vibration signal, a chemical signal, a mechanical signal, etc. In yet another and/or alternative embodiment of the present invention, a transmitter (e.g., wire, fiber optic cable, electromagnetic wave transmitter, etc.) is connected between the screw, nail or post, and/or head-piece, and at or near the surface of the patient's body and/or some other location, which transmitter allows a signal to be transmitted from a remote location to the screw, nail or post, and/or head-piece. In one aspect of this embodiment, the signal can a) transmit a signal to the mechanical or electrical device in the screw, nail or post, and/or head-piece; and/orb) provide instructions and/or programming to the mechanical or electrical device in the screw, nail or post, and/or head-piece. In still yet a further and/or alternative embodiment of the present invention, the mechanical and/or electrical device can be activated prior to, during, or after the insertion of the screw, nail or post, and/or head-piece in the bone and/or cartilage. In another and/or alternative aspect of this embodiment, one or more contact points are located at or near the surface of the skin of a human or animal, which one or more contacts are connected between a contact surface of the contact points and the screw, nail or post, and/or head-piece, and/or one or more components connected to the screw, nail or post, and/or head-piece. In still another and/or alternative aspect of this embodiment, the screw, nail or post, and/or head-piece, and/or one or more components connected to the screw, nail or post, and/or head-piece includes an electromagnetic wave transmitter and/or receiver which can send and/or receive signals in the form of electromagnetic waves. In still yet a further and/or alternative embodiment of the present invention, the mechanical and/or electrical device can be activated prior to, during, or after the insertion of the screw, nail or post, and/or head-piece in the bone and/or cartilage. In still a further and/or alternative embodiment of the invention, the mechanical and/or electrical device can at least partially control the location of substance discharge on the screw, nail or post, and/or head-piece; and/or control the amount and/or frequency of substance discharge on various regions of the screw, nail or post, and/or head-piece. In one aspect of this embodiment, the mechanical and/or electrical device can open and/or close one or more access openings, and/or cause one or more substances to flow into and/or out of one or more cavities. In still another and/or alternative embodiment, the amount of substance discharge from the screw, nail or post, and/or head-piece are at least about 0.001 milliliters per discharge, and generally about 0.002-20 milliliters per discharge; however, other discharge amounts can occur.

In still yet another and/or alternative aspect of the invention, the screw, nail or post, and/or head-piece includes one or more mechanical and/or electrical devices that at least partially cause the lower portion of the screw, nail or post to move relative to the head of the screw, nail or post, and/or cause the head-piece to move relative to head and/or lower portion of the screw, nail or post. The movement or the lower portion and head relative to one another, and/or the head-piece relative to the screw, nail or post allows for the length of the screw, nail or post, and/or the headpiece in combination with the screw, nail or post to increase and/or decrease in length. The change of length can be accomplished in a controlled manner (e.g., constant movement for a period of time, delayed movement, sequenced movement over a period of time, etc.). The mechanical device can include a motor and/or the like to cause the change in length. The electrical device can use electromagnetic forces or the like to cause the change in length. As can be appreciated, many other mechanical and/or electrical mechanisms can additionally or alternatively be used to change the length.

In still yet another and/or alternative embodiment of the present invention, the screw, nail or post, and/or head-piece is designed such that one or more cavities in the screw, nail or post, and/or head-piece can be filled and/or refilled with one or more substances after being inserted in position in a body. The filling and/or refilling of one or more cavities in the screw, nail or post, and/or head-piece facilitates in an ongoing or a sequence of therapies that can be applied at and/or contiguous to the site of insertion of the screw, nail or post, and/or head-piece. In one embodiment of the present invention, the screw, nail or post, and/or head-piece includes one or more access openings designed to receive an end of a syringe or other device that is adapted to insert a substance in the access opening. In another and/or alternative embodiment of the present invention, a tube is connected between the screw, nail or post, and/or head-piece and the surface of the patient's body, which tube includes an opening designed to receive an end of a syringe or other device adapted to insert a substance in the tube opening which in turn conveys the substance to an access opening in the screw, nail or post, and/or head-piece. In this particular design, an access tube is not required to extend from the screw, nail or post, and/or head-piece to a skin surface; require a portion of the screw, nail, post, head-piece and/or support system to be exposed at or above a skin surface; or require the cavity to be filled prior to closing a surgical area (see Tronzo U.S. Pat. No. 4,653,489 and Chappius U.S. Pat. No. 6,565,572 requiring filling prior to the closing the surgical site).

In still a further and/or alternative embodiment of the present invention, the screw, nail or post, and/or head-piece includes one or more mechanisms to promote bone healing on and/or about the screw, nail or post, and/or head-piece, and/or closely adjacent to the screw, nail or post, and/or head-piece. In one embodiment of the present invention, the screw, nail or post, and/or head-piece applies an electrical charge on or about the screw, nail or post, and/or head-piece. Electrical stimulation has been found, in certain situations, to promote the healing of bone and/or other tissue. The use of such electrical stimulation can promote the healing of bone and/or cartilage about the screw, nail or post, and/or head-piece. In another and/or alternative embodiment of the present invention, the screw, nail or post, and/or head-piece includes one or more mechanical and/or electrical devices that at least partially control the duration, timing and/or degree of electrical stimulation from the screw, nail or post, and/or head-piece. In one aspect of this embodiment, the mechanical and/or electrical device can be designed to control the duration, timing and/or degree of electrical stimulation based upon a preprogrammed sequence, as a function of time, and/or upon receipt of an external signal. In one non-limiting design, the mechanical and/or electrical device is preprogrammed to control the duration, timing and/or degree of electrical stimulation from the screw, nail or post, and/or head-piece. In one particular non-limiting design, the mechanical and/or electrical device includes a microchip that at least partially stores a program that allows and/or causes the occurrence of an electrical stimulation from the screw, nail or post, and/or head-piece. In another and/or alternative non-limiting particular design, the mechanical and/or electrical device includes one or more MEMS (micro-electro-mechanical systems). The MEMS includes both the preprogramming and the mechanism that allows and/or causes the occurrence of an electrical stimulation from the screw, nail or post, and/or head-piece. In still another and/or alternative non-limiting particular design, the microchip at least partially controls a separate mechanical and/or electrical device (e.g., battery, electric generator, etc.) which in turn allows and/or causes an electrical simulation to occur. In still another and/or alternative non-limiting particular design, the microchip can be preprogrammed and/or reprogrammed prior to, during and/or after the insertion of the screw, nail or post, and/or head-piece. As can be appreciated, the parameters for electrical stimulation can be altered by reprogramming (e.g., new data, additional data, new source code, additional source code, etc.) during the healing process of a patient, thus are individualized for a patient. Consequently, one or more settings for the mechanical and/or electrical device can be changed, as medical treatment needs dictate (e.g., greater or lesser stimulation, a more frequent electrical discharge, adjustments of time and/or power of electrical discharge, etc.). In yet another and/or alternative non-limiting particular design, the microchip can be activated prior to, during and/or after the insertion of the screw, nail or post, and/or head-piece. In another and/or alternative aspect of this embodiment, the external signal includes, but is not limited to, an electrical signal, a magnetic signal, an electromagnetic wave signal (e.g., light, radio wave, microwave, x-ray, infrared light, etc.), a heat signal, a vibration signal, a chemical signal, a mechanical signal, etc. In another and/or alternative embodiment of the invention, mechanical and/or electrical component can be charged prior to, during and/or after insertion of the screw, nail or post, and/or head-piece. In still another and/or alternative embodiment of the invention, mechanical and/or electrical component can be recharged after insertion of the screw, nail or post, and/or head-piece. In yet another and/or alternative embodiment of the present invention, a transmitter (e.g., wire, fiber optic cable, electromagnetic wave transmitter, etc.) is connected between the screw, nail or post, and/or head-piece and at or near the surface of the patient's body and/or some other location, which transmitter allows an electrical current and/or signal to be transmitted from a remote location to the screw, nail or post, and/or head-piece. In one aspect of this embodiment, the electrical current and/or signal can a) transmit a signal to the mechanical or electrical device in the screw, nail or post, and/or head-piece; b) recharge the mechanical and/or electrical device in the screw, nail or post, and/or head-piece; c) provide instructions and/or programming to the mechanical or electrical device in the screw, nail or post, and/or head-piece; d) generates and/or causes electrical simulation to be generated from the screw, nail or post, and/or head-piece. In another and/or alternative aspect of this embodiment, one or more contact points are located at or near the surface of the skin of a human or animal, which one or more contacts are connected between a contact surface of the contact points and the screw, nail or post, and/or head-piece, and/or one or more components connected to the screw, nail or post, and/or head-piece. In still another and/or alternative aspect of this embodiment, the screw, nail or post, and/or head-piece, and/or one or more components connected to the screw, nail or post, and/or head-piece, include an electromagnetic wave transmitter and/or receiver which can send and/or receive signals in the form of electromagnetic waves. In still yet a further and/or alternative embodiment of the present invention, the mechanical and/or electrical device can be activated prior to, during, or after the insertion of the screw, nail or post, and/or head-piece in the bone and/or cartilage. In a further and/or alternative embodiment of the invention, the electrical stimulation is at least partially generated by a battery, chemical reaction, generator, magnetic field, electric current, and/or the like. In still a further and/or alternative embodiment of the invention, the mechanical and/or electrical device can at least partially control the location of discharge on the screw, nail or post, and/or head-piece; and/or control the degree and/or frequency of discharge on various regions of the screw, nail or post, and/or head-piece. In one aspect of this embodiment, the mechanical and/or electrical device can relocate the location of electrical discharge on the screw, nail or post, and/or head-piece to promote healing in specified regions about the screw, nail or post, and/or head-piece. In another and/or alternative aspect of this embodiment, the mechanical and/or electrical device can regulate the amount of electrical discharge from one or more regions on the screw, nail or post, and/or head-piece to promote healing in specified regions about the screw, nail or post, and/or head-piece. In still another and/or alternative embodiment, the amount of voltage discharge from the screw, nail or post, and/or head-piece is at least about one microvolt per discharge, and generally about five microvolts to about 12 volts per discharge; however, other voltage amounts can be used. In yet another and/or alternative embodiment, the amount of current discharge from the screw, nail or post, and/or head-piece is at least about one microampere per discharge, and generally about two microamperes to about 0.1 amperes per discharge; however, other amperages can be used.

In yet a further and/or alternative aspect of the present invention, the screw, nail or post, and/or head-piece can be designed to be left in place for an indeterminate time after completion of surgery and post-surgical healing and/or can be removed at some time after the completion of surgery, or be replaced during ongoing therapy and/or treatment.

In still yet a further and/or alternative aspect of the present invention, the screw, nail or post, and/or head-piece is designed to be connected to a mechanical and/or electrical device which mechanical and/or electrical device at least partially regulates and/or controls the discharge of a substance and/or electrical current from at least a portion of the screw, nail or post, and/or head-piece. In one embodiment of the present invention, the mechanical and/or electrical device is connected to the screw, nail or post, and/or head-piece prior to, during or after insertion of the screw, nail or post, and/or head-piece. In another and/or alternative embodiment of the present invention, the mechanical and/or electrical device is detachable from the screw, nail or post, and/or head-piece prior to, during or after insertion of the screw, nail or post, and/or head-piece. In one aspect of this embodiment, the mechanical and/or electrical device can be replaced when it breaks, malfunctions, and/or has completed its useful life, without having to fully or partially remove the screw, nail or post, and/or head-piece. In still another and/or alternative embodiment of the present invention, the screw, nail or post, and/or head-piece includes one or more openings, connection locations, and/or contact points for the connection of one or more mechanical and/or electrical devices to the screw, nail or post, and/or head-piece. The one or more openings, connection locations, and/or contact points can function to secure the mechanical and/or electrical device to the screw, nail or post, and/or head-piece, and/or to integrate the mechanical and/or electrical device with one or more cavities and/or other mechanical and/or electrical devices in the screw, nail or post, and/or head-piece.

In another and/or alternative aspect of the present invention, the screw, nail or post, and/or head-piece is designed such that a mechanical and/or electrical device at least partially regulates and/or controls the discharge of a substance and/or electrical current from at least a portion of the screw, nail or post, and/or head-piece is at least partially formed and/or positioned in the screw, nail or post, and/or head-piece. In one embodiment of the present invention, the majority of the mechanical and/or electrical device is embedded in the screw, nail or post, and/or head-piece prior to, during or after insertion of the screw, nail or post, and/or head-piece. In another and/or alternative embodiment of the present invention, at least a portion of the mechanical and/or electrical device is connected to a portion of the mechanical and/or electrical device that is already at least partially formed and/or positioned in the screw, nail or post, and/or head-piece.

In still another and/or alternative aspect of the present invention, the screw, nail or post, and/or head-piece is formed of a substantially inert or biologically compatible material for use in humans. In one embodiment of the present invention, the screw, nail or post, and/or head-piece is designed to be used with a prosthetic implant that is designed to be placed in the intervertebral disc space that was formerly occupied by at least a portion of an intervertebral disc. In still another and/or alternative embodiment of the present invention, the prosthetic implant is designed to be readily inserted by established surgical procedures, with minimal chances of surgical difficulty. In yet another and/or alternative embodiment of the present invention, the screw, nail or post, and/or head-piece and/or head-piece includes, but is not limited to, bone (human and/or mammalian), stainless steel, titanium, chromemolybdenum, cobalt chromium alloy, chrome or chrome alloys, cobalt or cobalt alloys, polycarbonate, polypropylene, polyethylene, polymethylmethacrylate, polysolfone types filled with glass and/or carbon fibers, various types of carbon fiber (e.g., biocompatible carbon fiber, etc.), and/or fiber reinforced polymers. In one aspect of this embodiment, the material is wear resistant.

In accordance with yet another and/or alternative aspect of the present invention, the screw, nail or post, and/or head-piece includes one or more openings to facilitate in the positioning of the screw, nail or post, and/or head-piece relative to the bone or cartilage; to secure and/or detach the screw, nail or post in the bone and/or cartilage and/or to secure and/or detach the head-piece from the screw, nail or post. In one embodiment of the present invention, one or more of the openings in the screw, nail or post, and/or head-piece are adapted to receive an instrument for guiding, inserting, and/or removing the screw, nail or post, and/or head-piece. In one aspect of this embodiment, the one or more openings can be used to secure, lock, release and/or remove the head-piece to or from the screw, nail or post. In another and/or alternative embodiment of the present invention, the one or more openings can be designed to receive a wedge, shaft, screw, adhesive, etc. to at least partially connect and/or secure the head-piece to the screw, nail or post.

In accordance with still yet another and/or alternative aspect of the present invention, the screw, nail or post is at least partially connected to bone and/or cartilage after an opening in the bone and/or cartilage has been formed. Typically, the hole is formed by a drill or similar device. The size of the opening is typically selected to be smaller than the cross-sectional area of the screw, nail, or post; however, this is not required. The opening is typically inserted in the bone and/or cartilage to reduce damage to the bone and/or cartilage when the screw, nail or post is subsequently inserted in the bone and/or cartilage, and/or to provide a guide opening for insertion of the screw, nail or post, and/or head-piece. In one embodiment of the invention, a sleeve is inserted in the formed opening. The sleeve can be designed to be a temporary or permanent device. In one aspect of this embodiment, the sleeve is a temporary device that is designed to be at least partially inserted in an opening formed in a bone and then removed prior to the insertion of the screw, nail or post into the opening. In this design, the sleeve is used to a) inhibit or prevent contamination of the formed opening in the bone, b) inhibit or prevent growth of tissue and/or bone in the formed opening, and/or c) allow time for the bone and/or tissue around the opening to at least partially heal. As can be appreciated, other uses can be used for the temporary sleeve. In another and/or alternative aspect of this embodiment, the sleeve is a permanent device that is designed to be maintained in the opening formed in the bone. The sleeve will typically include a cavity that is designed to receive the screw, nail or post immediately after or shortly after the sleeve in inserted into the bone, or at some time after the sleeve has been inserted into the bone. The sleeve can be used to a) inhibit or prevent contamination of the formed opening in the bone, b) inhibit or prevent growth of tissue and/or bone in the formed opening, c) allow time for the bone and/or tissue around the opening to at least partially heal (e.g., 1-20 weeks) and/or d) facilitate in connecting or securing the screw, nail or post to the bone. As can be appreciated, other uses can be used for the permanent sleeve. In another and/or alternative embodiment of the invention, the sleeve can include and/or be at least partially coated with at least one substance (medicine and/or biological agent, etc.). The one or more substances can be used for a variety of reasons such as, but not limited to, improving the success of retaining the sleeve and/or screw, nail, or post in the bone and/or cartilage; reducing the rejection of the screw, nail or post, the headpiece, sleeve, and/or the support system after insertion in a body; reducing or inhibiting infection from the insertion of the screw, nail or post, the head-piece, the sleeve, and/or the support system after insertion in a body. As can be appreciated, the one or more substances can be used for other and/or additional reasons. In still another and/or alternative embodiment of the invention, the sleeve can be at least partially formed of a biodegradable material, a bioabsorable material, a non-biodegradable material, and/or a non-bioabsorable material. In yet another and/or alternative embodiment of the invention, the sleeve can include a removable cap. The cap can be used to at least partially cover or seal an internal cavity of the sleeve. This internal cavity can be used to a) contain one or more substances (e.g., medicine and/or other biological agents, etc.), b) facilitate in connecting a screw, nail, or post in the cavity, and/or c) facilitate in the insertion and/or removal of the sleeve into/from the bone. As can be appreciated, the sleeve can be used for other and/or additional reasons. The cap can include one or more slots, openings, ribs, threads, etc. to facilitate in the connection to and/or removal from the sleeve. In still yet another and/or alternative embodiment of the invention, the outer surface of the sleeve can include one or more ribs, spikes or barbs, threads, cavities, etc. to facilitate in the connection of the sleeve to the bone. In a further and/or alternative embodiment of the invention, the sleeve can include components (e.g., slots, ribs, openings, grooves, etc.) used to facilitate in the insertion and/or removal of the sleeve from the opening in the bone. In still a further and/or alternative embodiment of the invention, the sleeve can include one or more openings to facilitate in the flow of materials out of and/or into the sleeve, facilitate in exposing the surrounding tissue and/or bone to a current, etc. As can be appreciated, the one or more openings can be used for other and/or additional reasons. In still a further and/or alternative embodiment of the invention, the sleeve can have a uniform or non-uniform size and/or shape. The cross-sectional shape of the sleeve can be generally circular; however, other shapes can be used (e.g., circular, oval, polygonal, curvilinear, etc.). The sleeve can have a uniform or varied cross-sectional area along the longitudinal axis of the sleeve. In yet a further and/or alternative embodiment of the invention, the sleeve can be inserted at one period of time and surgery involving a screw, nail or post can be done at another period of time. In one non-limiting example, one or more sleeves can be inserted into one or more bones having openings formed therein. This procedure could be done by day surgery or outpatient surgery; however, longer visits could be required. After the one or more sleeves are inserted, the bone and tissue about the sleeve can be allowed to heal. If the sleeve is a semi-permanent or permanent sleeve, several weeks (e.g., 1-4 weeks) or months (e.g., 1-8 months) may be allowed to pass after the sleeve is inserted before further procedures involving the sleeve are conducted. Once a sufficient period of time has passed, a screw, nail or post can be inserted into the sleeve or the sleeve can be removed prior to the screw, nail or post being inserted into the bone. The procedure could also be done by day surgery or outpatient surgery; however, longer visits could be required. It is possible to use the sleeve to conveniently remove a support system from the vertebra or other regions in the body once the desired amount of healing has occurred. As such, screws, nails, rods, plates, shafts, etc. could be removed from the body and merely leave one or more sleeves behind. If the sleeves are bioabsorable or biodegradable, the sleeves are eventually eliminated from the body; otherwise the surrounding bone and/or tissue grows around and/or into the sleeve to incorporate the sleeve in the body. As a result, screws, nails, rods, plates, shafts, etc. can be conveniently removed from the body after their function is completed. The removal procedure could be done by day surgery or outpatient surgery; however, longer visits could be required. It is also and/or alternatively possible to use the one or more sleeves to allow the replacement of one or more screws, nails or posts that are being used for supplying and/or injecting one or more substances into and/or about a particular body region and/or being used to provide electro-stimulation into and/or about a particular body region. When such devices are used, the pump may fail and/or need to be replaced, one or more substances (e.g., medicine and/or biological agent, etc.) may need to be replenished and/or changed, the battery may fail and/or need to be replaced, and/or the screw, nail or post may need to be replaced. The use of a sleeve facilitates in the removal and insertion of a screw, nail or post out of and/or into the sleeve. The removal/insertion procedure could be done by day surgery or outpatient surgery; however, longer visits could be required.

In accordance with a further and/or alternative aspect of the present invention, there is provided a novel bone screw, nail or post (e.g., a screw, nail or post designed to be inserted into the pedicle structure of a vertebral body and/or other bones to provide load-bearing support and/or other medically beneficial purposes) which is designed and constructed in two or more components. The head of the bone screw, nail or post includes a male extension member or a female internal chamber to receive a head-piece. A band in a faceted, rough or cylindrical shape or other shape may be designed between the two threaded ends. The proximal end of the lower portion of the screw can have a machined non-tapered or tapered threaded end. The distal end can be machined to have either a male-threaded exterior or the head of the screw can have female-threaded interior of a set-size to allow a common family of attachments (here called "head-pieces") to be attached onto or into the threaded end or receptacle. The exterior or interior may be designed with a taper or not. The anchor of the head-piece can be machined with threaded, channeled or other receptacles to allow a head-piece having a machined cylindrical end, polyhedron end, etc. to be connectable to a complementary machined female internal chamber in the head of the screw, nail or post. Alternatively, the male extension member on the head of the bone screw, nail or post can be machined with threaded, channeled or other receptacles to allow the screw, nail or post to be connectable to a complementary machined connection cavity of the head-piece. The connection cavity can be used to receive a connection rod (e.g., a threaded rod) that can be threaded into the connection cavity of the head-piece at one end and threaded into a threaded female internal chamber in the head of the screw, nail or post. Set screws and/or other mechanical connection mechanisms (e.g., interior gripping, expanding locking inserts, etc.) can be used to facilitate in securing the head-piece to the screw, nail or post. The anchor or connection cavity of the head-piece, and/or the male extension member or the female internal chamber of the screw, nail or post can include one or more channels to facilitate in connecting the head-piece to the screw, nail or post, to facilitate in connecting one or more components of a support system to the head-piece and/or screw, nail or post; and/or contain substances, mechanical devices and/or electrical devices. The anchor of the head-piece can include a fork or one or more splits and also include an internal channel so that a "driver" (machined to fit within the channel) can cause portions of the anchor to expand. The driver can be screwed into the channel or forced in by mechanical pressure, forced by hydraulic means, etc. to cause the anchor to expand. The anchor could also or alternatively cause a force to be exerted on the screw, nail or post with results in a portion of the screw, nail or post to expand and/or buckle to facilitate in the securing of the screw, nail or post in the bone and/or cartilage. One or more channels in the head-piece and/or screw, nail or post can be filled with appropriate materials to facilitate and/or enhance bone growth. The appropriate materials can include, but are not limited to, (i) a polymer-based or other bone cement; (ii) expanded polymer or urethane foam; (iii) autologous growth compound, powdered bone or another compound of an appropriate biologic agent(s) or (iv) pharmaceuticals to diminish pain and/or stimulate bone growth or another material to accomplish an efficacious purpose related to the patient's recovery. The screw, nail or post and/or head-piece can include one or more channels, slots, ribs, etc. to permit and/or facilitate the introduction of one ore more substances for pain relief, to promote healing, for purposes of flexibility, for purposes of rigidity and/or for other beneficial purposes. The screw, nail or post and/or head-piece can include or be made of resorbable material so that, over a predetermined period of time, the portions thereof will be resorbed by the body. Alternatively, the screw, nail or post and/or head-piece can be made of non-resorbable material. The screw, nail or post and/or head-piece can be coated with a bioactive material to stimulate bone growth and/or to enhance fixation of the screw, nail or post and/or head-piece in place. The present invention provides a variety of sizes of head-pieces to meet specific surgical needs, and all of the head-pieces are designed so that the head-pieces have a commonly-sized threaded anchor or connection cavity so as to be connected to a commonly-sized female internal chamber or male extension member, respectively of a screw, nail or post thereby creating a family of head-pieces that can be connected to a screw, nail or post. As such a variety of sizes and shapes of head-pieces used to meet specific surgical needs can all be connected to a single type or family of screw, nail or post, thus significantly limiting the number of components required for a surgical procedure and significantly simplifying a particular surgical procedure. The head-pieces can have many different designs and configurations to perform various functions. Some of these designs include, but are not limited to, a tower designed with an exterior threaded shaft (of varying lengths, as would be desired by orthopedic surgeons) so as to permit attachment of spinal plates and other medical devices, a closed-rod connector, an open rod connector, a cross connector, a universal polyaxial connector, a rod device, a plate device, a rod and plate device, a wire fixation device, an artificial ligament "facet", and the like. The screw, nail or post and/or head-piece can be coated with a bioactive material to stimulate bone growth and/or to enhance fixation of the anchor into the bone. Special tooling can be designed and used to facilitate the insertion and/or removal of the head-piece; the insertion and/or removal of the screw, nail or post, and/or the expansion of the lower portion of the screw, nail or post and/or expansion of the anchor of the head-piece. In the most common applications of the invention, one head-piece will be utilized and inserted into the head of one screw, nail or post that has been inserted into a vertebra in the spinal column. The head-piece will be used in conjunction with the screw, nail or post to provide support to a damaged or injured disc or vertebra that is repaired or partially or wholly removed during a surgical process. The bone screw, nail or post will be inserted and fixed in a location to avoid intrusion into the spinal cord area while at the same time avoiding extending outside the vertebral column. During the course of treatment, as medical results and opinion dictate, one or more alternative head-pieces may be substituted for the original head-piece attached to the screw, nail or post in the initial surgery to provide an alternative method of treatment or to respond to changed conditions (either as a result of surgery, progress of disease or otherwise). This placement will be optimized utilizing one or more of the configurations described hereinabove. The screw, nail or post and/or head-piece can be made of a sterilized and shaped bone (human and/or mammalian), of a polymer or of biocompatible carbon fiber, a reinforced polymer and/or alternately or additionally made of traditional orthopedic implant materials such as, but not limited to, titanium, chrome cobalt, stainless steel, etc.

It is an object of the present invention to provide an improved screw, nail or post for insertion into bone and/or cartilage.

It is another and/or alternative object of the present invention to provide a screw, nail or post that can be easily and efficiently positioned into bone and/or cartilage and which reduces the failure rate of prosthetic implants.

It is still another and/or alternative object of the present invention to provide a screw, nail or post that can be connected to a set or family of head-pieces.

It is yet another and/or alternative object of the present invention to provide a screw, nail or post that can have the head-piece changed before, during and/or after a course of treatment, as medical results and opinion dictates, to provide an alternative method of treatment, and/or to respond to changed conditions (either as a result of surgery, progress of disease or otherwise).

It is yet another and/or alternative object of the present invention to provide a screw, nail or post, and/or head-piece which are relatively small and which can be readily manipulated.

It is still yet another and/or alternative object of the present invention to provide a screw, nail or post, and/or head-piece that can be manufactured with present conventional technology.

It is a further and/or alternative object of the present invention to provide a screw, nail or post, and/or head-piece that are designed to simplify the insertion and fixing of a support system.

It is still a further and/or alternative object of the present invention to provide a screw, nail or post, and/or head-piece that are relatively easy to manufacture and cost effective to manufacture.

It is yet a further and/or alternative object of the present invention to provide a screw, nail or post, and/or head-piece that include one or more cavities which are used to alter the weight distribution of the screw, nail or post, and/or head-piece; alter the structural integrity, flexibility and/or rigidity of the screw, nail or post, and/or head-piece; to at least partially contain a substance such as, but not limited to, a material that a) promotes and/or inhibits bone and/or other tissue growth, b) inhibits rejection of the screw, nail or post, and/or head-piece, c) inhibits rejection of components connected to and/or located adjacent to the screw, nail or post, and/or head-piece, d) reduces infection, e) reduces inflammation, f) reduces pain, g) provides vitamins, minerals, and/or nutrients, h) provides genetic material, i) provides tissue, j) facilitates in the insertion, positioning, and/or removal of the screw, nail or post, and/or head-piece (e.g. lubricant, Teflon, graphite, etc.), k) secures the screw, nail or post, and/or head-piece (e.g., bone cement or other adhesive, etc.), l) promotes healing of surrounding tissue, m) combats cancer and/or other diseases, n) combats and/or cures biological abnormalities (e.g., a chemical imbalance, etc.), o) functions as a location and/or visual indicator, and/or the like, and/or to at least partially contain one or more electrical and/or mechanical components.

It is still yet a further and/or alternative object of the present invention to provide a screw, nail or post, and/or head-piece that includes at least one cavity that has at least one access opening to the surface of the screw, nail or post, and/or head-piece.

It is another and/or alternative object of the present invention to provide a screw, nail or post, and/or head-piece that allows for insertion of one or more substances into one or more cavities of the screw, nail or post, and/or head-piece; that allows one or more substances to exit the one or more cavities of the screw, nail or post, and/or head-piece; and/or that allows body fluids and/or bone growth into the one or more access openings and/or into the one or more cavities.

It is still another and/or alternative object of the present invention to provide a screw, nail or post, and/or head-piece that allows a physician to insert one or more substances into one or more cavities prior to, during, and/or after the insertion of the screw, nail, or post, and/or head-piece in the bone and/or cartilage.

It is yet another and/or alternative object of the present invention to provide a screw, nail or post, and/or head-piece that includes a cap and/or cover that are applied over one or more access openings which are designed to at least partially seal one or more substances in the one or more cavities, and/or to at least partially control the release of one or more substances from the one or more cavities.

It is still yet another and/or alternative object of the present invention to provide a screw, nail or post, and/or head-piece that includes one or more outer surface regions that are coated with one or more substances.

It is a further and/or alternative object of the present invention to provide a screw, nail or post, and/or head-piece that include one or more mechanical and/or electrical devices that at least partially control the release of one or more substances from the screw, nail or post, and/or head-piece.

It is still a further and/or alternative object of the present invention to provide a screw, nail or post, and/or head-piece that are designed such that one or more cavities can be filled and/or refilled with one or more substances after being inserted in bone and/or cartilage.

It is yet a further and/or alternative object of the present invention to provide a screw, nail or post, and/or head-piece that apply an electrical charge on or about the screw, nail or post, and/or head-piece.

It is yet a further and/or alternative object of the present invention to provide a sleeve that can be at least partially inserted into an opening in bone and/or tissue and can be used to facilitate in the removal and/or insertion of the screw, nail or post from/into the sleeve.

It is still yet a further and/or alternative object of the present invention to provide a sleeve that can be at least partially inserted into an opening in bone and/or tissue and allowed to at least partially adhere to the bone and/or tissue over a period of time prior to insertion of the screw, nail or post from/into the sleeve.

It is another and/or alternative object of the present invention to provide a sleeve that can be used to facilitate in the removal of a screw, nail or post from the sleeve and/or insertion of a replacement screw, nail or post from/into the sleeve.

These and other objects of the invention will become apparent to those skilled in the art upon reading and understanding the following detailed description of preferred embodiments taken together with the drawings.

BRIEF DESCRIPTION OF THE DRAWINGS

The invention may take physical form in certain parts and arrangement of parts, preferred embodiments of which will be described in detail and illustrated in the accompanying drawings which form a part hereof and wherein.

DESCRIPTION OF THE PREFERRED EMBODIMENTS

Figure 1:
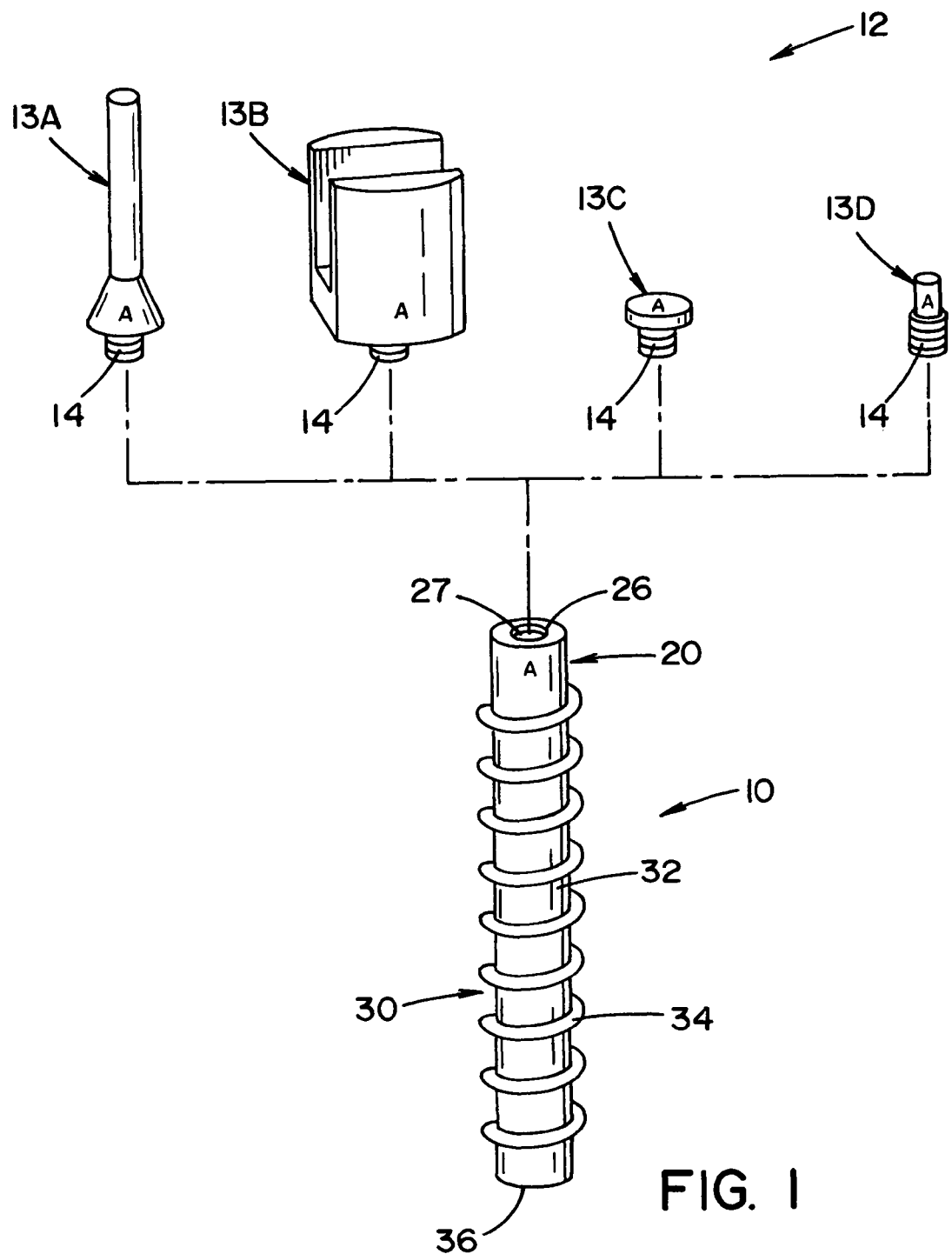
FIG. 1 is a perspective view of a prosthetic screw and several head-pieces that can be threaded into a female internal chamber of the head of the prosthetic screw.

Referring to the drawings, wherein the showings are for the purpose of illustrating the preferred embodiment of the invention only and not for the purpose of limiting same, FIG. 1 illustrates a novel bone screw system for insertion into bone and/or cartilage of a vertebrae. The bone screw system will be described with particular reference for use with surgical procedure involving the vertebrae and will be thus referred to as a pedicle screw system; however, it will be appreciated that the bone screw system can be used in other regions of a body (e.g., leg, arm, hand, foot, knee, hip, pelvis, rib cage, skull, etc.) to promote healing in such regions. It will also be appreciated that the bone screw system can be used in other areas of the vertebrae such as, but not limited to, the laminna, facets, etc.

Orthopaedic surgeons, as well as neurosurgeons, have long recognized the need for the use of pedicle screws in the treatment of spinal pathologies, deformities and traumas. The pedicle screws are typically placed in the vertebral pedicle since this area has been long recognized as the "force nucleus" of the spinal vertebra, i.e., the area of the spine where a force applied to the bone by the pedicle screw would have the highest mechanical advantage in repositioning the bone. The pedicle screw can be used by a surgeon in other procedures, such as anchoring tissue or in bone plating systems.

Referring again to FIG. 1, the pedicle screw system includes a pedicle screw 10 and a plurality of head-pieces. The pedicle screw 10 is fabricated of biocompatible material and has a head 20 and a lower portion 30. The particular material or materials selected will generally depend on the location of the pedicle screw and the various objectives to be accomplished by the pedicle screw. The exterior surface of the head is illustrated as smooth; however, the outer surface can include one or more indentations, slots, ridges, openings, etc. Head 20 is also illustrated as having a circular cross-sectional shape. As can be appreciated, other shapes can be used (e.g., octagonal, hexagonal, triangular, square, oval, etc.). The top of the head includes an opening 26 that provides access to a female internal chamber 27. The lower portion 30 of the pedicle screw includes an outer surface 32 that includes thread 34. The cross-sectional shape of the lower portion is substantially circular and has a substantially constant cross-sectional shape and cross-sectional area throughout the longitudinal length of the lower portion. The end 36 of the lower portion has a substantially flat configuration. Head-pieces 12 include a top portion 13 and an anchor 14. The anchor 14 of each of the different head-pieces has the same sized and shaped threaded anchor and can be threaded into the threaded female internal chamber 27. As a result, many different head-pieces can be connected to the pedicle screw prior to, during and/or after the pedicle screw is inserted into the pedicle. The various top portions 13A-D can be used to insert the pedicle screw into the pedicle (e.g., 13D), cap opening 26 (e.g., 13C), connect various type of rods, plates, etc. to the pedicle screw (e.g., 13A, 13B, 13D, etc.). As can be appreciated, the top portions of the head-pieces illustrated in FIG. 1 are illustrative of the many configurations that can be used in the present invention. Each of the head-pieces includes a marking "A" to indicate the family or type of head-piece that can be connected to pedicle screw 10. Pedicle screw 10 also includes a marking "A" that indicates the type or family of pedicle screw that can be used with a type of family of head-piece. This marking system facilitates in the use of the pedicle screw system.

Figure 2:
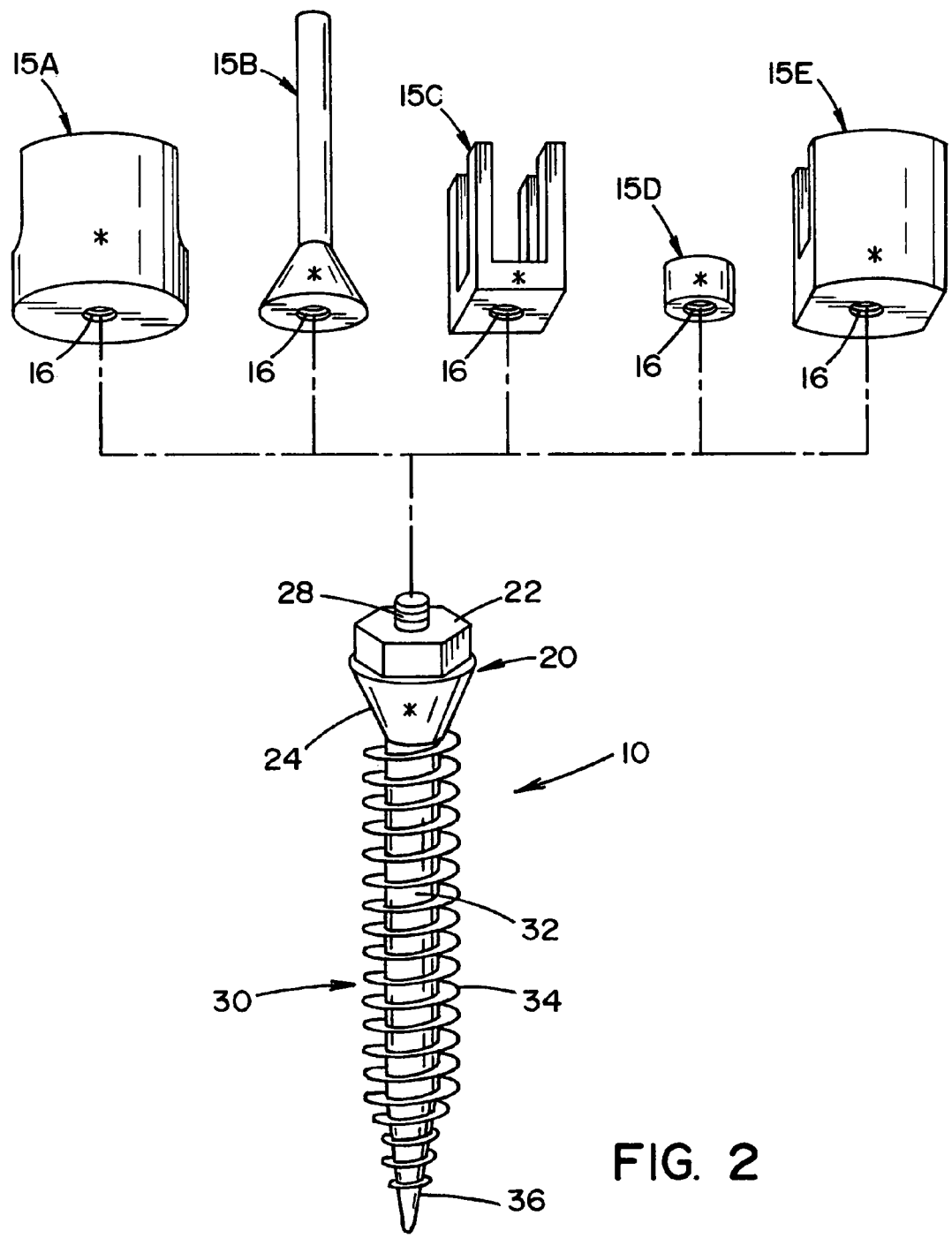
FIG. 2 is a perspective view of a prosthetic screw and several head-pieces that can be threaded onto a threaded male extension member of the head of the prosthetic screw.

Referring now to FIG. 2, there is illustrated another pedicle screw system in accordance with the present invention. This pedicle screw system includes a pedicle screw 10 and a plurality of head-pieces 15A-E. The pedicle screw 10 is fabricated of biocompatible material and has a head 20 and a lower portion 30. The particular material or materials selected will generally depend on the location of the pedicle screw and the various objectives to be accomplished by the pedicle screw. The head includes a hexagonal shaped cross-section 22 that facilitates in the insertion of the pedicle screw into the pedicle. The head 22 can include one or more indentations, slots, ridges, openings, etc. to further facilitate in the insertion of the pedicle screw into the pedicle. The top of the head includes a threaded male extension member 28. Positioned below the hexagonal section is a conical shaped portion 24 that terminates at the lower portion 30 of the pedicle screw. The lower portion 30 of the pedicle screw includes an outer surface 32 that includes thread 34. The cross-sectional shape of the lower portion is substantially circular and has a substantially constant cross-sectional shape and cross-sectional area throughout the majority of the longitudinal length of the lower portion. The end 36 of the lower portion tapers to a point. As can be appreciated, many other shapes and/or configurations of the head and/or lower portion can be used for the pedicle screw in the present invention. Head-pieces 15 include a connection cavity 16. Each connection cavity of each head-piece has the same size and shape so that it can be threaded onto the threaded male extension member 28 of the pedicle screw. As a result, many different head-pieces can be connected to the pedicle screw prior to, during and/or after the pedicle screw is inserted into the pedicle. The various head-pieces 15A-E can be used to cap the male extension member 28 (e.g., 15D), connect various type of rods, plates, etc. to the pedicle screw (e.g., 15A, 15B, 15C, 15E, etc.), etc. As can be appreciated, the top portions of the head-pieces illustrated in FIG. 2 are illustrative of the many configurations that can be used in the present invention. Each of the head-pieces includes a marking "*" to indicate the family or type of head-piece that can be connected to pedicle screw 10. Pedicle screw 10 also includes a marking "*" that indicates the type or family of pedicle screw that can be used with a type of family of head-piece. This marking system facilitates in the use of the pedicle screw system. As can be appreciated, many other types of markings can be used.

The support systems illustrated in FIGS. 1 and 2 can significantly simplify a surgical procedure. Prior to surgical procedure, the doctor uses various non-evasive techniques or mildly evasive techniques to determine the scope of the damage to the vertebra (e.g., MRI, X-ray, Ultrasound, scope, etc.). Although this preliminary analysis is very helpful in determining the scope of damage and a proposed methodology to fix the damage, circumstances can change during the actual surgical procedure. The vertebra may be more or less damaged than believed, thus requiring a change of procedure and a require a different pedicle system arrangement than first thought. The change in a pedicle system can cause problems during a surgical procedure since in the past certain pedicle screws having specific head configurations were used to connect certain components of the pedicle system. When the pedicle system is changed, different pedicle screws are required to form the new pedicle system. If a change in the pedicle system is required after the produce has begun, previously inserted pedicle screws may have to be removed and new screws inserted to accommodate the different pedicle system. The removal of previously inserted pedicle screws can cause further damage to a vertebra and/or cause significant delay in a surgical procedure. If the pre-inserted pedicle screws cannot be removed without concern for further damage to the vertebra, the existing pedicle screws must be left in and a less than optimal pedicle system must be formed. The pedicle screws of the present invention overcome this problem since head-pieces 13 or 15 can be simple exchanged for another type of head-piece to accommodate a change in the pedicle system to be used. As a result, if a change must be made to a pedicle system during a surgical procedure, the previously inserted pedicle screws can be simply capped if not needed or a new head-piece can be inserted on the head of the pedicle screw to accommodate the new pedicle system configuration. The pedicle screw system of the present invention also reduces the number of components that a hospital or other medical facility needs to maintain in inventory, and also reduces the number of components for the pedicle system that need to be brought to a surgical procedure. The universal mounting system for the head-pieces enables a single pedicle screw to be used with many different components of a pedicle system.

In utilizing the pedicle screw system, the pedicle screw is typically inserted into the bone and/or cartilage that includes a tap or pre-drilled hole formed therein as a guide for the placement of the screw. The bone has a relatively hard compact shell, which encases a loose spongy cancellous bone material. The tap or pre-drilled hole facilitates in the insertion of the pedicle screw into the bone and/or minimizes damage to the bone during the insertion of the pedicle screw. Typically the tap or pre-drilled hole has a diameter that is less than the threads 34 on the lower portion 30 of the pedicle screw. For example, the tap or pre-drilled hole may have a diameter of about 8 mm, and the threads on the lower portion of the pedicle screw have a diameter of about 8.5 mm. The tap hole or pre-drilled hole forms a precise, preset path of insertion for the pedicle screw. Since the threads have a larger diameter that the opening in the bone and/or cartilage, the thread 34 bites into the bone and/or cartilage thereby accurately positioning the pedicle screw in the bone and/or cartilage and securing the pedicle screw in the bone and/or cartilage. Typically the pedicle screw is adapted for use in securing a tower designed with an exterior threaded shaft, spinal plates, a closed-rod connector, an open rod connector, a cross connector, a universal polyaxial connector, a rod device, a plate device, a rod and plate device, a wire fixation device, an artificial ligament "facet", and the like.

Figure 3:
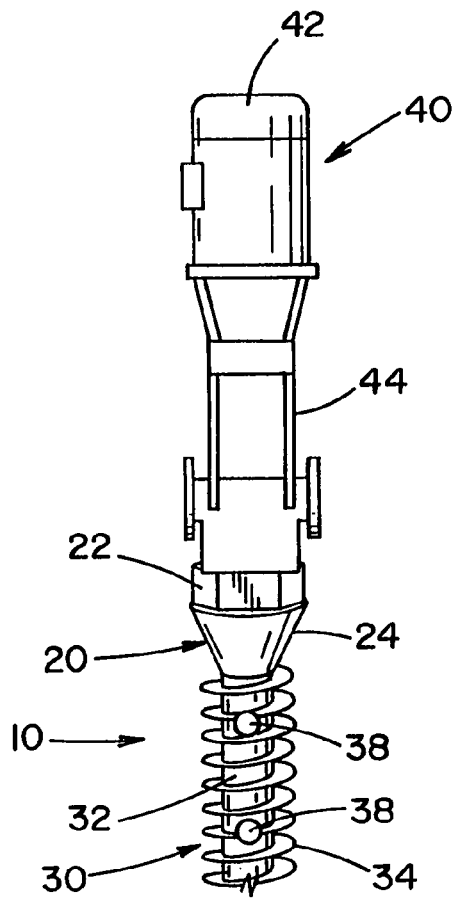
FIG. 3 is a partial perspective view of the front side prosthetic screw which includes a head-piece having a mechanical mechanism connected to top of the prosthetic screw.

Referring now to FIG. 3, another type of head-piece is illustrated. The head-piece is a mechanical mechanism 40. The mechanical mechanism can include a connection cavity to receive a male extension member 28 on the head of the screw as shown in FIG. 2, or can include a threaded anchor that is threadably inserted into the female internal chamber 27 of the pedicle screw shown in FIG. 1. The connection is designed to allow the mechanical mechanism to be at least partially connected and/or removably connected to the head prior to, during, and/or after the pedicle screw has been inserted into the pedicle.

Figure 4:
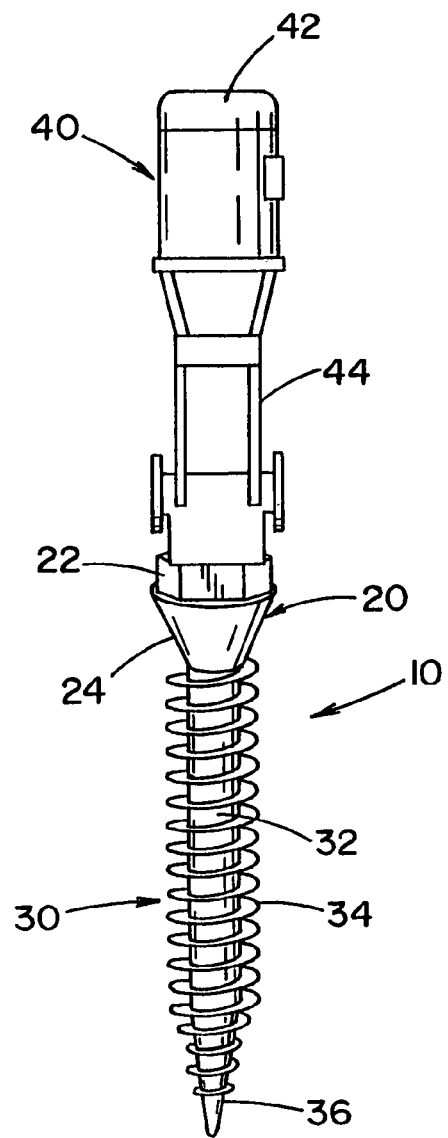
FIG. 4 is a perspective view of the back side of the prosthetic screw of FIG. 3.

As illustrated in FIGS. 3 and 4, mechanical mechanism 40 includes a pump or motor 42 and a cylinder 44 that are connected between pump or motor 42 and top section 22 of head 20. The pump or motor can have any number of different configurations and/or can operate in any number of different ways. The pump orientation illustrated in FIGS. 3 and 4 can facilitate the use of this embodiment in regions of the spine wherein the orientation of the pump as illustrated in FIGS. 1 and 2 may interfere with the surrounding tissue. As can be appreciated, pump 42 can be orientated in a variety of other manners to facilitate the use of the pump and successful use of the pedicle screw. The pump or motor can be designed to cause a substance contained in the cylinder to flow out of the cylinder, cause the head of the pedicle screw to move relative to the lower portion, cause the mechanical mechanism to move relative to the pedicle screw, cause the pedicle screw and/or mechanical mechanism to vibrate, etc. In one non-limiting configuration, the pump includes a piston that at least partially travels into the cylinder to cause one or more substances in the cylinder to flow out of the cylinder. The mechanical mechanism can be activated to cause one or more substances in the cylinder to flow out of the cylinder and/or to perform one or more other operations. The activation of the mechanical mechanism can be manual and/or by a preprogrammed activation mechanism. When the mechanical mechanism includes a pump, the rate at which the pump causes one or more substances in the cylinder to flow out of the cylinder can be constant or manually and/or electronically regulated to vary over time. When the mechanical mechanism includes a motor to move one or more portions of the pedicle screw and/or head-piece relative to one another, the rate at which the motor causes movement can be constant or manually and/or electronically regulated to vary over time. As illustrated in FIG. 3, the lower portion 30 of pedicle screw 10 includes two openings 38. As can be appreciated, more or fewer openings can be located in the lower portion. Furthermore, it can be appreciated that one or more openings can be located in the head of the pedicle screw. The openings are designed to allow at least a portion of the one or more substances in the cylinder 44 to flow out of the openings 38 and to the surrounding bone and/or cartilage. The head of the pedicle screw can include one or more channels, not shown, which allows the one or more substances from the cylinder 44 to flow into the one or more channels in the head, not shown.

As can be appreciated, the one or more channels in the head of the pedicle screw can be additionally or alternatively located in the male extension member 28 or in the female internal chamber 27. These one or more channels in the head allow the one or more substances to flow through the head and into one or more channels in the lower portion, not shown, and out through openings 38. The two or more openings 38 can be positioned on the same side of the pedicle screw as illustrated in FIG. 3, or positioned in the lower portion in other manners. The mechanical mechanism is illustrated as oriented along the longitudinal axis of the pedicle screw. As can be appreciated, at least a portion of the mechanical mechanism can be arranged at one or more angles relative to the longitudinal axis of the pedicle screw (e.g., perpendicular, 30°, 45°, 60°, etc.).

Figure 5:
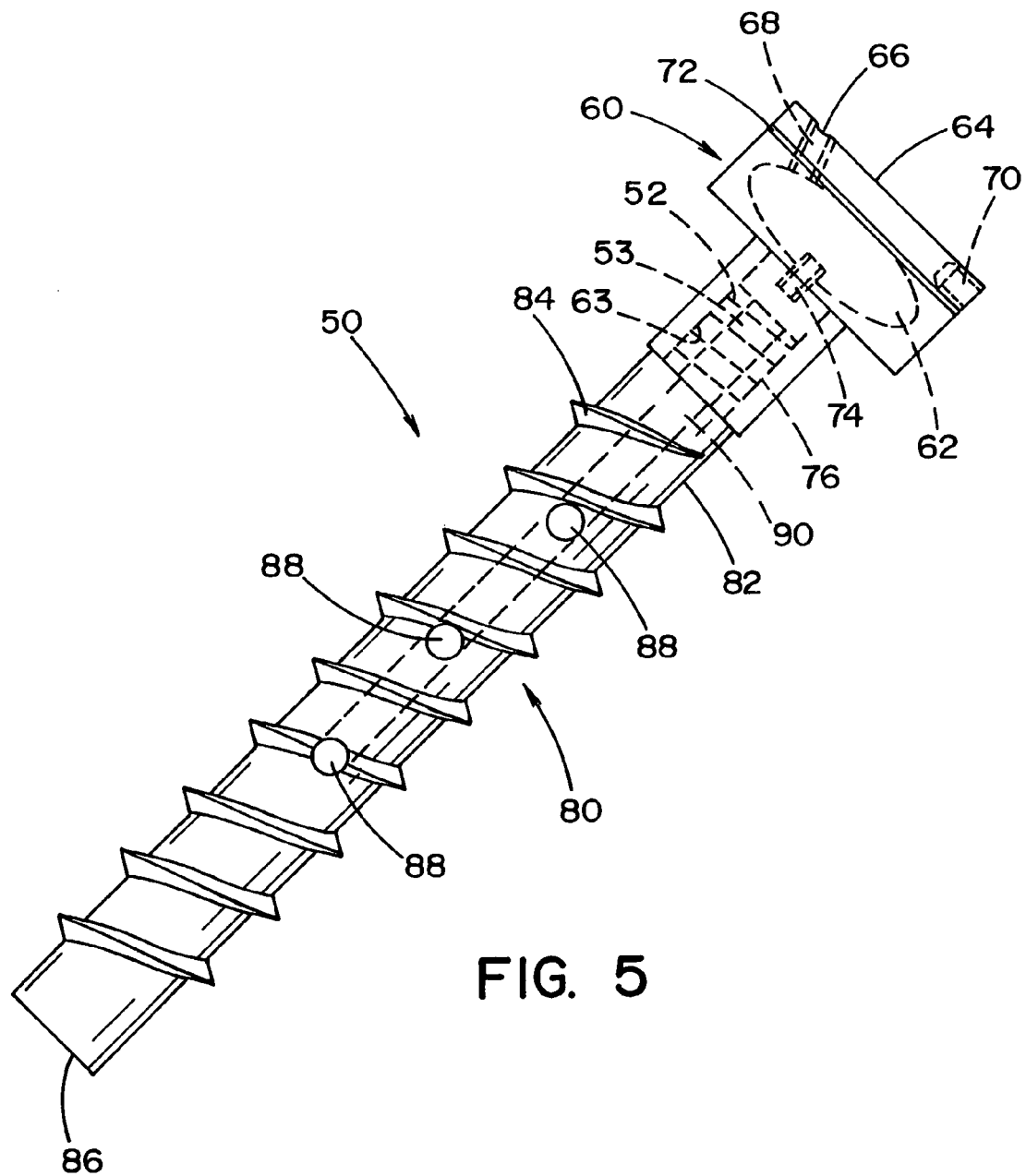
FIG. 5 is another perspective view of the front side of the prosthetic screw which includes a head-piece having a mechanical mechanism positioned in the top of the prosthetic screw.

Referring now to FIG. 5, pedicle screw 50 includes a thread 52 that is threaded into a connection cavity 63 of head-piece 60. The cross-section of head-piece 60 illustrates that the head-piece includes one or more reservoirs 62 for containing one or more substances described above. The reservoir is illustrated as having an ovoid shape; however, other shapes can be used. The top 64 of head-piece 60 includes one or more port openings 66. Port opening 66 allows one or more substances to be inserted and/or removed from reservoir 62. One or more port passages 68 allows fluid passage between port opening 66 and reservoir 62. The port opening may have a sealing member to inhibit or prevent one or more substances in the reservoir from freely flowing out of the reservoir and out through port opening 66. One or more motors 70 are positioned in head-piece 60. Motor 70 can be any type of motor that is small enough to be substantially fully positioned in the head. One non-limiting motor is a MEMS device. The head-piece also includes one or more pressure plates 72 designed to be moved by motor 70 to thereby cause the one or more substances in reservoir 62 to flow out of the reservoir. One or more discharge ports 74 allow one or more substances to flow from the reservoir and into a base chamber 76 of head-piece 60. As can be appreciated, motor 70 can be designed to perform other or additional functions (e.g., vibrations, moving one or more components relative to one another, etc.). The lower portion 80 of the pedicle screw includes an outer surface 82 that includes thread 84. The cross-sectional shape of the lower portion is substantially circular and has a substantially constant cross-sectional shape and cross-sectional area throughout the majority of the longitudinal length of the lower portion. The end 86 of the lower portion is substantially flat. As can be appreciated, many other shapes and/or configurations of the head and/or lower portion can be used for the pedicle screw (e.g., tapered end, etc.). The lower portion also includes three openings 88. As can be appreciated, more or fewer openings can be located in the lower portion (e.g., opening in the end, etc.). The openings are designed to allow at least a portion of the one or more substances to flow out of the openings 88 and to the surrounding bone and/or cartilage. The lower portion also includes one or more channels 90 to allow the one or more substances to flow from reservoir 62 and into connection cavity 63, through channel 53 of threaded male extension member 52, into channel 90 in the lower portion and out through openings 88. The two or more openings can be positioned on the same side of the pedicle screw as illustrated in FIG. 5, or be positioned in other locations. The mechanical mechanism is designed to be fully or partially embedded under the skin after completion of a surgical procedure. The mechanical mechanism can be designed to be permanently left in the body, or be removed from the body after performing its function. As stated above, once the pedicle screw is connected to the bone and/or cartilage, the mechanical mechanism can be activated so that the pump causes one or more substances to flow out of openings 88. The mechanical mechanism can alternatively be activated prior to complete insertion of the pedicle screw into the bone and/or cartilage. The activation of the mechanical mechanism can be manual and/or by a preprogrammed activation mechanism. The rate at which the pump causes one or more substances in the cylinder to flow out of the cylinder can be constant or be manually and/or electronically regulated to vary over time.

Figure 6:
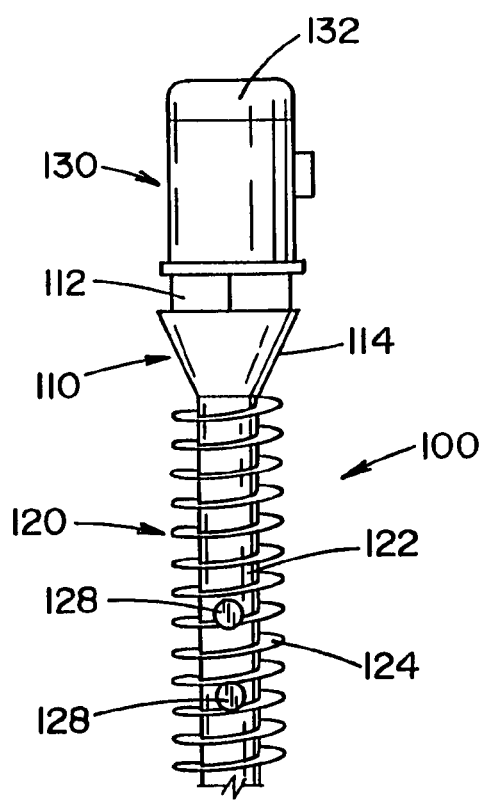
FIG. 6 is a partial perspective view of the front side of the prosthetic screw which includes a head-piece having an electrical mechanism connected to top of the prosthetic screw.
Figure 7:
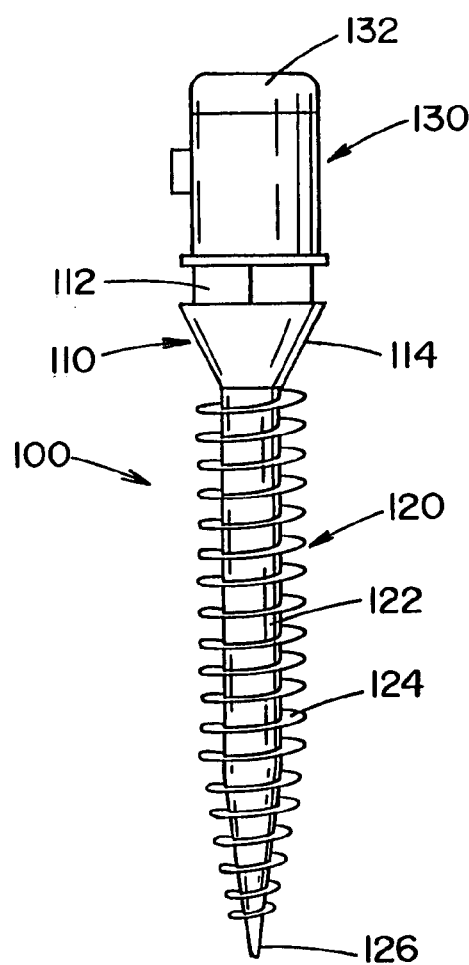
FIG. 7 is a perspective view of the back side of the prosthetic screw of FIG. 8.

Referring now to FIGS. 6 and 7, pedicle screw 100 includes a head 110 and a lower portion 120. Head 110 has a hexagonal cross-sectional shaped top section 112 to facilitate in the insertion of the pedicle screw into the pedicle. As can be appreciated, other shapes of the top section can be used. As can also be appreciated, the top section 112 can include one or more indentations, slots, ridges, openings, etc. to facilitate in the insertion of the pedicle screw into the pedicle. Positioned below the hexagonal top section is a conical shaped portion 114 that terminates at the lower portion 120 of the pedicle screw. The lower portion of the pedicle screw includes an outer surface 122 that includes thread 124. The cross-sectional shape of the lower portion is substantially circular and has a substantially constant cross-sectional shape and cross-sectional area throughout the majority of the longitudinal length of the lower portion. The end 126 of the lower portion as illustrated in FIG. 7 tapers to a point; however, the end 126 can have a substantially flat configuration and/or have a non-tapering configuration. As can be appreciated, many other shapes and/or configurations of the head and/or lower portion can be used for the pedicle screw in the present invention. A head-piece 130 in the form of an electrical mechanism 130 is connected to top section 112 of head 110. The head-piece is threaded onto the head of the pedicle screw; however, the head-piece can be connected to the pedicle screw in other or additional means (e.g., screw, bolt, solder, weld, latch, snap, clip, etc.). The head-piece can be at least partially connected to and/or removed from the head of the pedicle screw prior to, during, and/or after the pedicle screw has been inserted into the pedicle. The electrical mechanism can include a battery or electric generator 132. The battery or electric generator can have any number of different configurations and/or can operate in any number of different ways. The battery or electric generator can be designed to supply an electric current to one or more surfaces of the pedicle screw. In one non-limiting configuration, the electrical mechanism includes a battery to supply electric current to one or more regions on the pedicle screw. Once the pedicle screw is connected to the bone and/or cartilage, the electrical mechanism can be activated so that the battery or electric generator begins suppling electric current to one or more regions on the pedicle screw. The electrical mechanism can alternatively be activated prior to complete insertion of the pedicle screw into the bone and/or cartilage. The activation of the electrical mechanism can be manual and/or by a preprogrammed activation mechanism. The time period, current level and/or voltage level at which the electrical mechanism discharges electric current can be constant or manually and/or electronically regulated to vary over time. The lower portion 120 of pedicle screw 100 includes two electrodes 128. As can be appreciated, additional electrodes can be located in the lower portion. Furthermore, it can be appreciated that one or more electrodes can be located in the head of the pedicle screw. The electrodes are designed to conduct electrical current about the surrounding bone and/or cartilage. The head of the pedicle screw includes one or more regions, not shown, which allow current to be conducted between the battery or electric generator and the two or more electrodes in the lower portion. For example, the one or more regions can be a passageway for containing and electrically conducting material such as, but not limited to, a wire. The two or more electrodes can be positioned on the same side of the pedicle screw as illustrated in FIG. 6, or be positioned in the lower portion in other manners. The electrical mechanism is designed to be fully or partially embedded under the skin after completion of a surgical procedure. The electrical mechanism can be designed to be permanently left in the body, or be removed from the body after performing its function.

Figure 8:
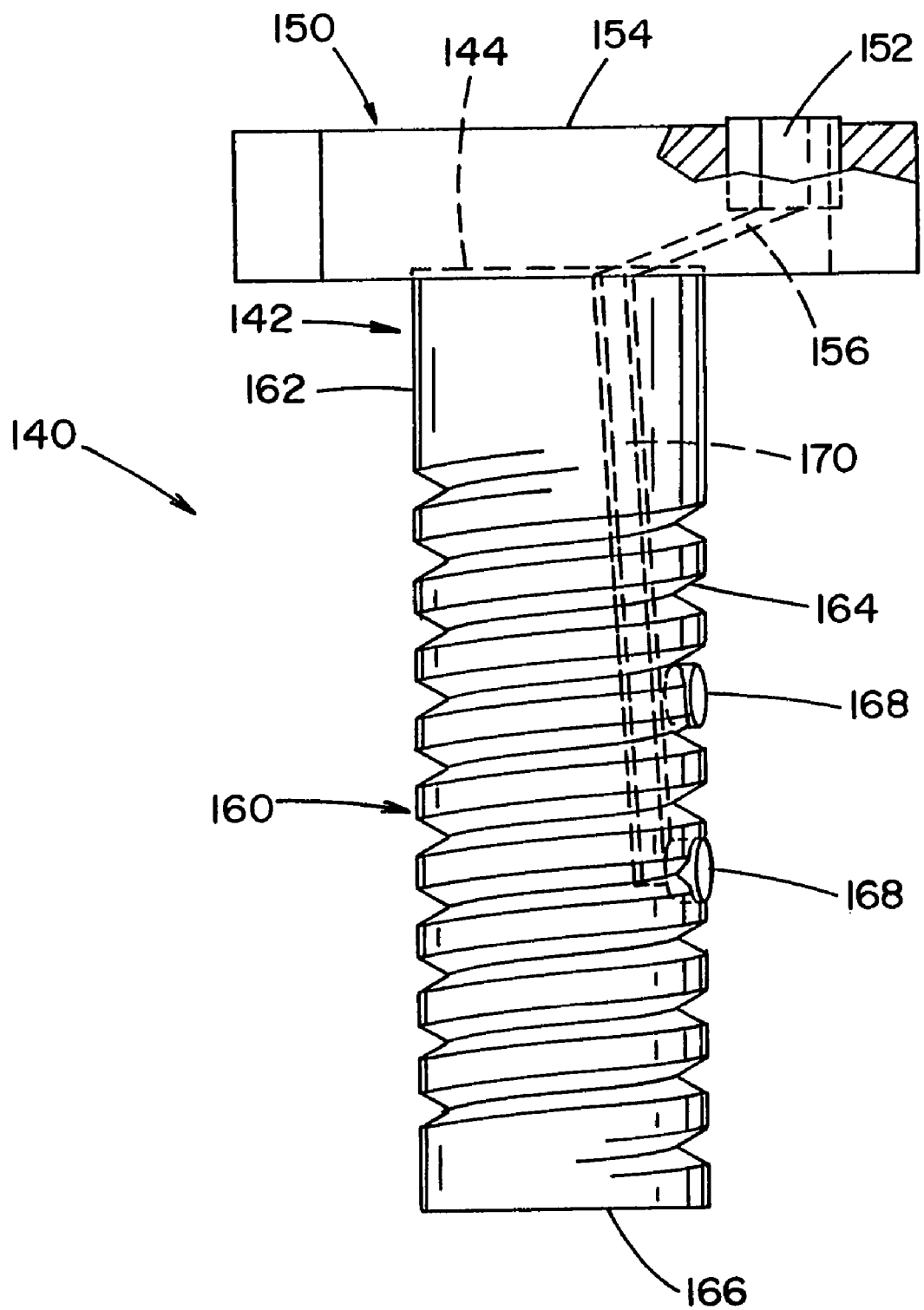
FIG. 8 is another perspective view of the front side of the prosthetic screw which includes a head-piece having an electrical mechanism positioned in the top of the prosthetic screw.

Referring now to FIG. 8, pedicle screw 140 includes a head 142 and a lower portion 160. Connected to the top of head 142 is a head-piece 150. The head-piece is threaded onto thread 144 of head 142. Head-piece 150 includes a battery 152 positioned in top surface 154. The battery is illustrated as having a cubical shape; however, other shapes can be used. The head-piece has a rectangular shape; however, other shapes can be used. The battery can be connected in the head-piece in a variety of manners. The battery can also be connected such that the battery can be periodically replaced. A channel 156 is positioned under the battery and travels between the battery and head 142. The channel continues into lower portion 160 of the pedicle screw. Typically a wire or other electrical conductor is positioned in the channel. The discharge rate, the discharge duration, etc. of the battery can be constant or electronically controlled.

The lower portion 160 of the pedicle screw includes an outer surface 162 that includes thread 164. The cross-sectional shape of the lower portion is substantially circular and has a substantially constant cross-sectional shape and cross-sectional area throughout the majority of the longitudinal length of the lower portion. The end 166 of the lower portion is substantially flat. As can be appreciated, many other shapes and/or configurations of the head and/or lower portion can be used for the pedicle screw. The lower portion also includes two electrodes 168. As can be appreciated, more electrodes can be located in the lower portion. Furthermore, it can be appreciated that one or more electrodes can be located in the top portion of the pedicle screw. The electrodes are designed to conduct current between the electrodes and to the surrounding tissue. The lower portion also includes one or more channels 170 wherein an electrical conductor is positioned. Channel 170 enables an electrical conductor to connect the electrodes 168 to the electrical conductor in channel 156. The electrodes can be positioned on the same side of the pedicle screw as illustrated in FIG. 8, or positioned on the lower portion in other manners. Once the pedicle screw is connected to the bone and/or cartilage, the electrical mechanism can be activated so that the battery conducts a current between the electrodes. The electrical mechanism alternatively can be activated prior to complete insertion of the pedicle screw into the bone and/or cartilage. The activation of the electrical mechanism can be manual and/or by a preprogrammed activation mechanism. The discharge rate at which the battery conducts current between the electrodes can be constant or manually and/or electronically regulated to vary over time.

Figure 9:
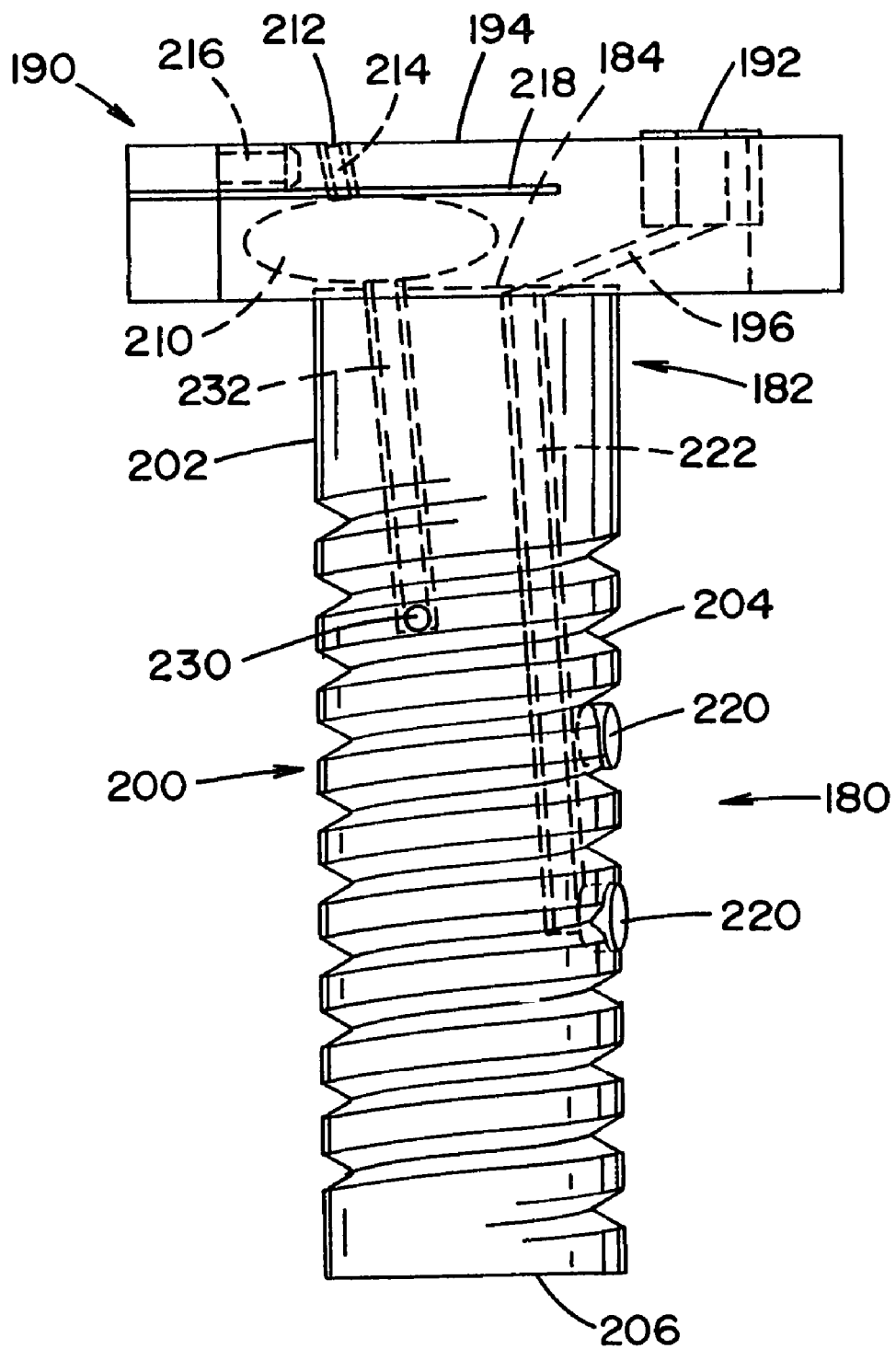
FIG. 9 is another perspective view of the front side of the prosthetic screw which includes head-piece having an electrical mechanism and a mechanical mechanism positioned in the top of the prosthetic screw.

Referring now to FIG. 9, pedicle screw 180 includes a head 182 and a lower portion 200. Connected to the top of head 182 is a head-piece 190. The head-piece is threaded onto thread 184 of head 182. Head-piece 190 includes a battery 192 positioned in top surface 194. The battery configuration is similar to that of FIG. 8. As explained with respect the pedicle screw in FIG. 8, the battery can be connected in the head in a variety of manners. The battery can also be connected such that the battery can be periodically replaced. A channel 196 is positioned under the battery and travels between the battery and lower portion 200 of the pedicle screw. Typically a wire or other electrical conductor is positioned in the channel. The discharge rate, the discharge duration, etc. of the battery can be constant or electronically controlled. Head-piece 190 also includes one or more reservoirs 210 for containing one or more substances described above. The reservoir is illustrated as having an ovoid shape; however, as explained with respect to FIG. 5, other shapes can be used. The top of head-piece 190 includes one or more port openings 212 to allow one or more substances to be inserted and/or removed from the reservoir. One or more port passages 214 allows fluid passage between port opening 212 and reservoir 210. The port opening can be designed similar to the port opening described with respect to FIG. 5. One or more motors 216 are positioned in head-piece 190. The motor design, type and configuration can be similar to the motor disclosed in FIG. 5. The head-piece also includes one or more pressure plates 218 designed to be moved by the motor to cause the one or more substances in the reservoir to flow out of the reservoir. One or more discharge ports 220 allow one or more substances to flow from the reservoir. The lower portion 200 of the pedicle screw includes an outer surface 202 that includes thread 204. The cross-sectional shape of the lower portion is substantially circular and has a substantially constant cross-sectional shape and cross-sectional area throughout the majority of the longitudinal length of the lower portion. The end 206 of the lower portion is substantially flat. As can be appreciated, many other shapes and/or configurations of the head and/or lower portion can be used for the pedicle screw. The lower portion also includes two electrodes 220. As can be appreciated, more electrodes can be located in the lower portion. Furthermore, it can be appreciated that one or more electrodes can be located in the head of the pedicle screw. The electrodes are designed to conduct current between the electrodes and the bone and/or surrounding tissue. The lower portion also includes one or more channels 222 wherein an electrical conductor is positioned. Channel 222 enables an electrical conductor to connect the electrodes 220 to the electrical conductor in channel 196. The electrodes can be positioned on the same side of the pedicle screw as illustrated in FIG. 8, or positioned on the lower portion in other manners. The lower portion 200 of the pedicle screw also includes an opening 230. As can be appreciated, more openings can be located in the lower portion. Furthermore, it can be appreciated that one or more openings can be located in the head of the pedicle screw. The opening is designed to allow at least a portion of the one or more substances to flow out of the opening and to the surrounding bone and/or cartilage. The lower portion also includes one or more channels 232 to allow the one or more substances to flow from the reservoir and out through opening 230. The operation of the motor to cause the one or more substances to flow out through opening 230 can be similar to the manner discussed with respect to FIG. 5. Once the pedicle screw is connected to the bone and/or cartilage, the electrical mechanism can be activated so that the battery conducts a current between the electrodes. The electrical mechanism alternatively can be activated prior to complete insertion of the pedicle screw into the bone and/or cartilage. The activation of the electrical mechanism can be manual and/or by a preprogrammed activation mechanism. The discharge rate at which the battery conducts current between the electrodes can be constant or be manually and/or electronically regulated to vary over time. Furthermore, the mechanical mechanism can be activated to cause one or more substances in the cylinder to flow out of the cylinder and/or to perform one or more other operations. The activation of the mechanical mechanism can be manual and/or by a preprogrammed activation mechanism. When the mechanical mechanism includes a pump, the rate at which the pump causes one or more substances in the cylinder to flow out of the cylinder can be constant or manually and/or electronically regulated to vary over time. When the mechanical mechanism includes a motor to move one or more portions of the pedicle screw and/or head-piece relative to one another, the rate at which the motor causes movement can be constant or manually and/or electronically regulated to vary over time.

The pedicle screw and/or head-piece can be at least partially coated with and contain in one or more cavities a substance that includes one or more materials that promote bone and/or other tissue growth, inhibit rejection of the prosthetic implant, reduce infection, reduce inflammation, reduce pain, promote healing of surrounding tissue, function as a location and/or visual indicator, and/or the like. Such substances include, but are not limited to, antithrombogenic agents; steroids; thioprotese inhibitors; antimicrobials; antibiotics; tissue plasma activators; monoclonal antibodies; antifibrosis compounds; hormones; growth factors; anti-mitotic agents; immunosuppressive agents; sense or antisense oligonucleotides; nucleic acid analogues; inhibitors of transcription factor activity; anti-neoplastic compounds; chemotherapeutic compounds; radioactive agents; growth factors; antiplatlet compounds; antitabolite compounds; anti-inflammatory compounds; anticoagulent compounds; antimitotic compounds; antioxidants; antimetabolite compounds; anti-migratory agents; anti-matrix compounds; anti-vital compounds; anti-proliferatives; anti-fungal compounds; anti-protozoal compounds; human tissue; animal tissue; synthetic tissue; human cells, animal cells; synthetic cells; and/or bone-stimulation, bone-growth and/or bone activating matter.

Figure 10:
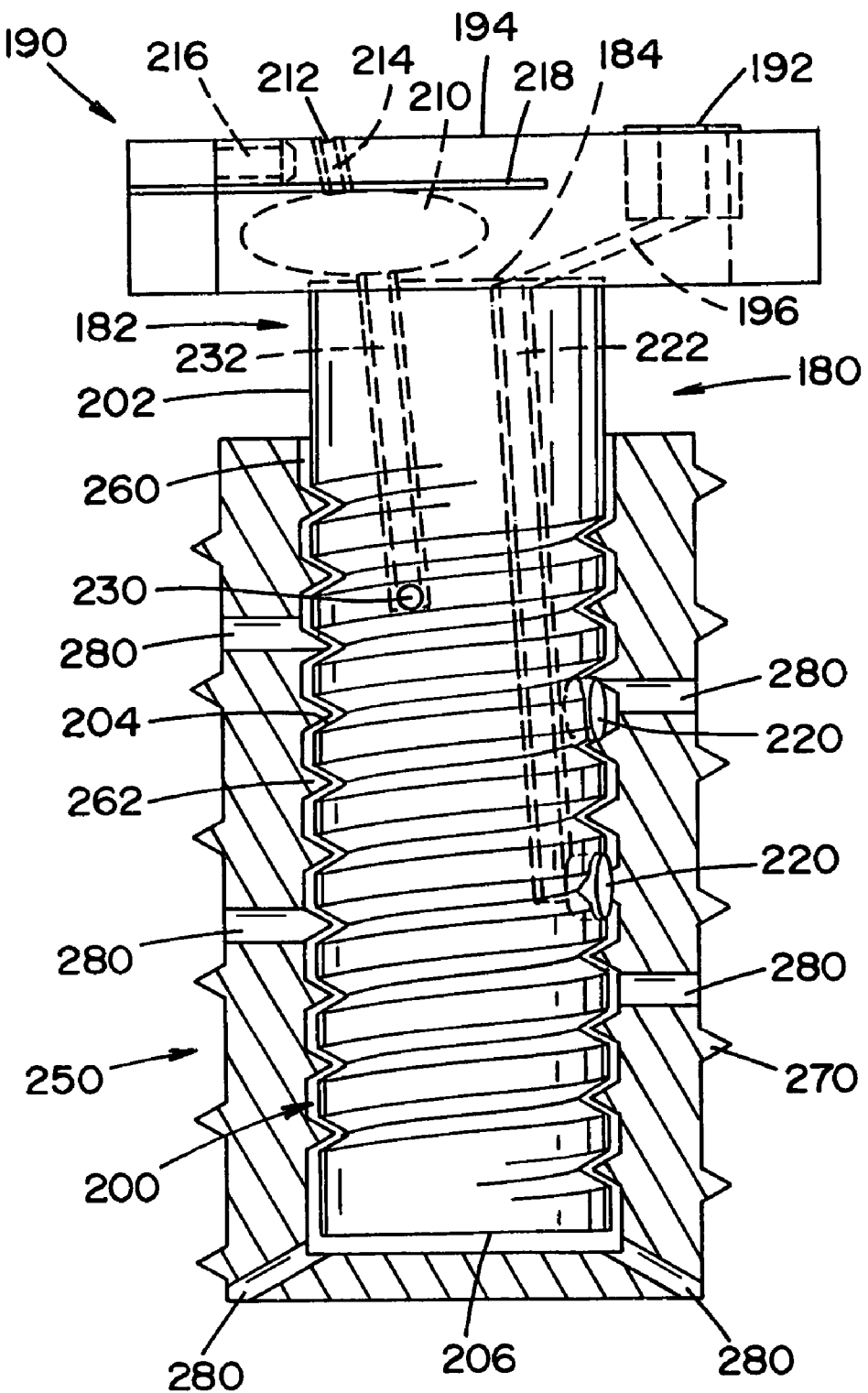
FIG. 10 is a perspective view of the front side of the prosthetic screw that is shown in a cut away portion of a sleeve; and, FIG. 11 is perspective view of the front side of the sleeve shown in FIG. 10.
Figure 11:
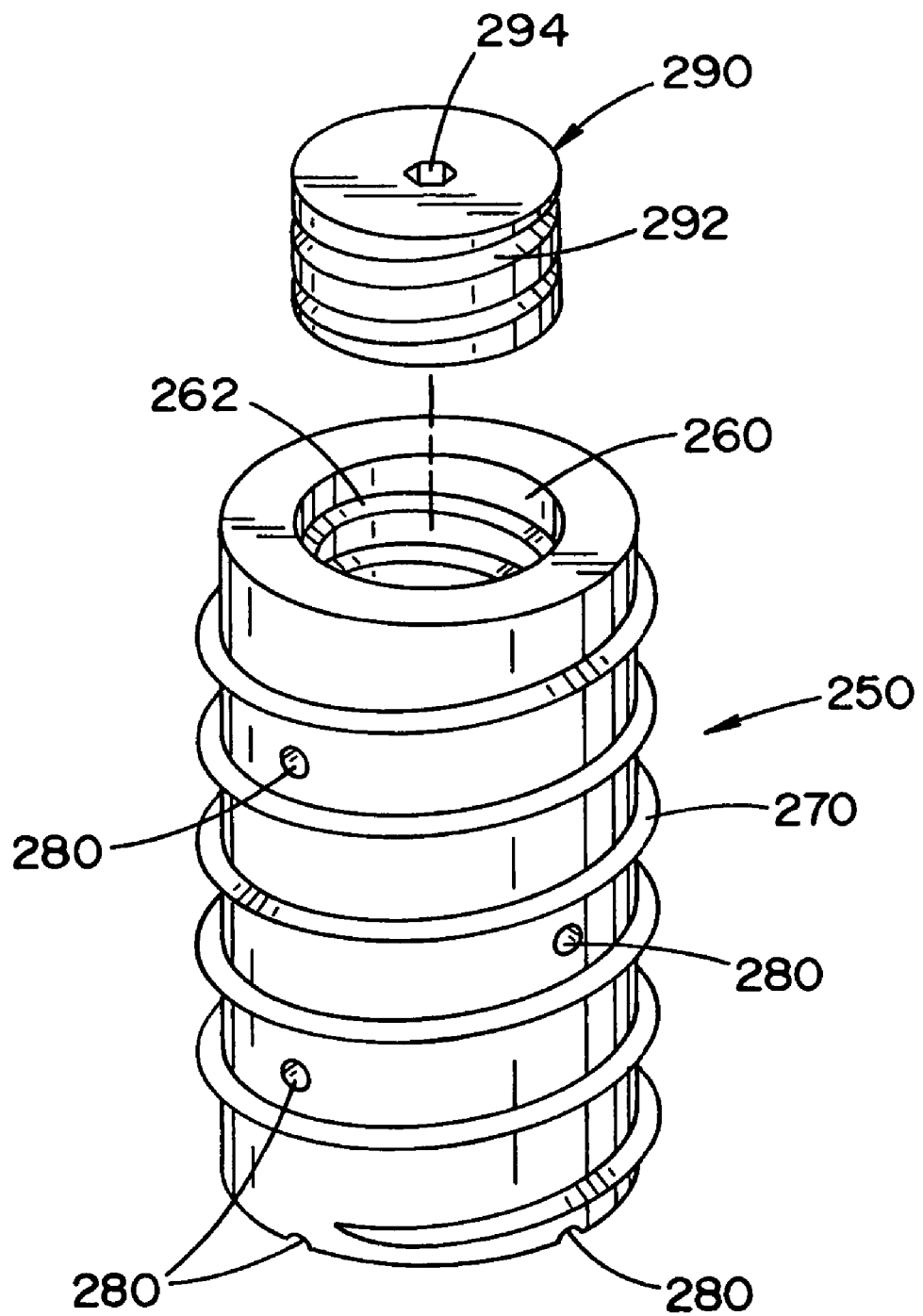

Referring now to FIG. 10, there is illustrated the pedicle screw of FIG. 9 inserted in a sleeve 250. Sleeve 250 without the pedicle screw is illustrated in FIG. 11. The sleeve is illustrated as having a substantially uniform circular cross-sectional shape; however, it can be appreciated that other shapes can be used. The sleeve includes a central cavity 260 that is designed to receive pedicle screw 180. The central cavity includes threads 262 that are designed to engage thread 204 on lower portion 200 of pedicle screw 180. The threads in the central cavity and on the pedicle screw enable the pedicle screw to be threaded into and/or removed from the sleeve. As can be appreciated, other and/or additional mechanisms can be used to facilitate in securing the pedicle screw in the sleeve. Sleeve 250 is illustrated as including a threaded outer surface 270. Threads 270 are designed to facilitate in anchoring the sleeve in an opening in the bone. As can be appreciated, the outer surface can have other and/or additional surface configurations to facilitate in anchoring the sleeve in an opening in the bone. As can also be appreciated, the outer surface can be smooth. Sleeve 250 is also illustrated as including several openings 280. Openings 280 as designed to enable fluids to flow into and/or out of the interior of sleeve 250. For instance, when the pedicle screw is designed to inject and/or secrete one or more substances into and/or about the bone, the openings allow the one or more substances to flow out of the sleeve. Openings 280 can alternatively or additionally be used to enable tissue and/or bone to secure to the sleeve so as to facilitate in anchoring the sleeve in an opening in the bone. The openings can also be used to facilitate in the exposure of the surrounding tissue to electrical stimulation by the pedicle screw when the pedicle screw is designed to discharge such electro-stimulation. A cap 290 can be used in conjunction with the sleeve. The cap includes threads 292 that are designed to be threaded onto threads 262 in central cavity 260. The cap also includes an opening 294 that is used to insert and/or remove the cap from the sleeve. The outer surface of the sleeve can be coated with one or more substances to facilitate in the success of the sleeve being used in the bone.

The use of the sleeve can facilitate various types of medical procedures. For instance, the sleeve can be used to enable easier extraction and/or replacement of the pedicle screw in a bone. In this procedure, the pedicle screw may to designed to secrete various substances and/or electro-stimulation. Over a period of time the pedicle screw may need to be replaced so as to replenish the pedicle screw with additional substances and/or replace the pedicle screw having a replenished supply of one or more substances. Alternatively and/or additionally, the pedicle screw may need to be replaced so as to recharge the pedicle screw with for further electro-stimulation treatments and/or replace the pedicle screw having a pedicle screw having a new power supply. Alternatively, the use of the pedicle screw may be completed and need to be removed from the bone. In these situations, the sleeve facilitates in the removal and/or replacement of the pedicle screw in the bone.

The simplicity of the insertion and/or removal of the pedicle screw from the sleeve can lend such procedure to outpatient or day surgery (e.g., doctor's office, ambulatory surgery center, etc.). The procedure could be designed to merely involve minor micro-invasive surgery. As a result, the use of the sleeve could reduce the cost to the patient and much of the inconvenience to the patient.

The sleeve could be inserted in a patient by forming an opening in the bone and then inserting the sleeve in the opening. The sleeve can then be left in the bone for a sufficient period of time until the sleeve is properly anchored to and/or set in the bone. This initial procedure could lend itself to being performed by outpatient or day surgery in a doctor's office, ambulatory surgery center, etc. This minor micro-invasive surgery could be performed in a shorter time and at a lower cost than in a hospital for an extended stay. After the sleeve has become properly set and/or anchored in the bone, a second procedure could be performed to insert the pedicle screw into the sleeve. Once again, this procedure could also lend itself to being performed by outpatient or day surgery in a doctor's office, ambulatory surgery center, etc.

When the sleeve is inserted on the bone and allowed to set and/or anchor to the bone prior to inserting the pedicle screw in the bone, a cap 290 can be used at the end of the sleeve to at least partially inhibit bone or tissue from growing in the top of the sleeve, which growth could interfere with the later insertion of the pedicle screw. At the time the pedicle screw is to be inserted in the sleeve, the cap 290 is removed from the sleeve and the pedicle screw is then inserted into the sleeve. As can be appreciated, if the pedicle screw is to be inserted in the sleeve shortly after the sleeve is inserted in the opening in the bone, the use of the cap can be eliminated; however, this is not required.

As can also be appreciated, the insertion of the sleeve maybe performed by outpatient or day surgery in a doctor's office, ambulatory surgery center, etc., and the insertion of the pedicle screw can be inserted by some extended surgical procedure in a hospital, especially if the insertion of the pedicle involves a more complex produce and/or is part of some larger procedure (e.g., the insertion of a stabilizing system, etc.).

The invention has been described with reference to the preferred embodiments. These and other modifications of the preferred embodiments as well as other embodiments of the invention will be obvious from the disclosure herein, whereby the foregoing descriptive matter is to be interpreted merely as illustrative of the invention and not as a limitation. It is intended to include all such modifications and alterations insofar as they come within the scope of the appended claims.

I claim:

1. A bone implant system to connect bone, cartilage, or combinations thereof to a support system comprising a set of head-pieces and a screw, nail or post, said screw, nail or post having a head and lower portion, said head portion of said screw, nail or post including a head connector, said set of head-pieces including a plurality of different head-pieces, each of said head-pieces in said set of head-pieces including an upper portion and a head-piece connector, said head-piece connector for each of said head-pieces having a similar configuration and designed to be secured to said head connector on said head portion of said screw, nail or post, at least one of said head-pieces at least partially connected below said upper portion of said head-piece, a plurality of said head-pieces in said set of head-pieces having a differently configured upper portion designed to connect to differing components of said support system, said head connector includes a female internal chamber, each of said head-piece connectors of said head-pieces includes male extension member, said female internal chamber designed to at least partially telescopically be received in said male extension member of said head-pieces and thereby connecting said head-pieces to said head portion.

2. The bone implant system as defined in claim 1, wherein said head connector includes a male extension member, each of said head-piece connectors of said head-pieces includes a connection cavity and a connection arrangement in said connection cavity, said male extension member designed to be at least partially telescopically received in said connection cavity and connect to said connection arrangement in said connection cavity of each of said head-piece.

3. The bone implant system as defined in claim 2, wherein said male extension member includes at least one thread and said connection arrangement of said connection cavity includes at least one corresponding thread.

4. The bone implant system as defined in claim 1, wherein said male extension member includes at least one thread and said female internal chamber includes at least one corresponding thread.

5. The bone implant system as defined in claim 1, wherein said lower portion includes at least one thread.

6. The bone implant system as defined in claim 1, wherein at least one of said head-pieces includes a mechanical mechanism, an electrical mechanism or combinations thereof.

7. The bone implant system as defined in claim 6, wherein said lower portion includes at least one interface designed to at least partially discharge an electrical current, a medical substance or combinations thereof.

8. The bone implant system as defined in claim 1, wherein said lower portion, head, head-piece or combinations thereof are at least partially including a coating material, said coating material including a compound that facilitates in the insertion, securing, or combinations thereof of the lower portion in said bone, cartilage, or combinations thereof; promotes, inhibits, or combinations thereof bone, other tissue growth, combinations thereof; inhibits rejection of said bone implant; inhibits rejection of components connected to said bone implant, located adjacent to said bone implant, or combinations thereof; reduces infection; reduces inflammation; reduces pain; promotes healing of surrounding tissue; combats cancer, other diseases, or combinations thereof; combats biological abnormalities; functions as a location indicator; functions as a visual indicator; or combinations thereof.

9. The bone implant system as defined in claim 1, wherein said lower portion, head, head-piece or combinations thereof at least partially includes at least one medical substance.

10. The bone implant system as defined in claim 9, wherein said medical substance includes at least one antithrombogenic agent, steroid, thioprotese inhibitor, antimicrobial, antibiotic, tissue plasma activator, monoclonal antibody, antifibrosis compound, hormone, growth factor, anti-mitotic agent, immunosuppressive agent, sense or antisense oligonucleotide, nucleic acid analogue, inhibitor of transcription factor activity, anti-neoplastic compound, chemotherapeutic compound, radioactive agent, growth factor, antiplatlet compound, antitabolite compound, anti-inflammatory compound, anticoagulent compound, antimitotic compound, antioxidant, antimetabolite compound, anti-migratory agent, anti-matrix compound, anti-vital compound, anti-proliferative, anti-fungal compound, anti-protozoal compound, human tissue, animal tissue, synthetic tissue, human cells, animal cells, synthetic cells, bone-stimulation matter, bone-growth matter, bone activating matter or combinations thereof.

11. The bone implant system as defined in claim 1, wherein said lower portion, head or combinations thereof are at least partially biodegradable.

12. The bone implant system as defined in claim 1, wherein said head-pieces are at least partially biodegradable.

13. The bone implant system as defined in claim 1, wherein at least one of said head pieces in said set of head-pieces having an upper portion that includes a connection tower with an exterior threaded shaft, a closed-rod connector, an open rod connector, a cross connector, a universal polyaxial connector, a spinal plate connector, a wire fixation device, or an artificial ligament "facet", at least two of said head pieces in said set of head-pieces having different upper portions.

14. The bone implant system as defined in claim 13, wherein a plurality of said head pieces in said set of head-pieces having an upper portion that includes a connection tower with an exterior threaded shaft, a closed-rod connector, an open rod connector, a cross connector, a universal polyaxial connector, a spinal plate connector, a wire fixation device, or an artificial ligament "facet", at least two of said head pieces in said set of head-pieces having different upper portions.

15. The bone implant system as defined in claim 1, including a sleeve, said sleeve including an opening designed to receive at least a portion of said lower portion of said screw, nail or post.

16. A bone implant system to connect bone, cartilage, or combinations thereof to a support system comprising a set of head-pieces and a screw, nail or post, said screw, nail or post having a head and lower portion, said head portion of said screw, nail or post including a head connector, said set of head-pieces including a plurality of different head-pieces, each of said head-pieces in said set of head-pieces including an upper portion and a head-piece connector, said head-piece connector for each of said head-pieces having a similar configuration and designed to be secured to said head connector on said head portion of said screw, nail or post, at least one of said head-pieces at least partially connected below said upper portion of said head-piece, a plurality of said head-pieces in said set of head-pieces having a differently configured upper portion designed to connect to differing components of said support system, both said head-pieces and said screw, nail or post include a marking to indicate that said head-pieces and said screw, nail or post belong to a same family or type.

17. A bone implant system to connect bone, cartilage, or combinations thereof to a support system comprising a head-piece and a screw, nail or post, said screw, nail or post having a head and lower portion, said head portion of said screw, nail or post including a head connector, said head-piece including a head-piece connector and an upper portion, said upper portion designed to connect to at least one component of said support system, said lower portion of said head-piece connector designed to connect to said head connector of said head portion of said screw, nail or post, said head-piece and said screw, nail or post both including a marking to indicate that said head-piece and said screw, nail or post belong to the same family or type.

18. The bone implant system as defined in claim 17, wherein said head connector includes a male extension member and said head-piece connector of said head-piece includes a connection cavity and a connection arrangement in said connection cavity, said male extension member designed to be at least partially telescopically received in said connection cavity and connect to said connection arrangement in said connection cavity of said head-piece.

19. The bone implant system as defined in claim 18, wherein said male extension member includes at least one thread and said connection arrangement of said connection cavity includes at least one corresponding thread.

20. The bone implant system as defined in claim 17, wherein said head connector includes a female internal chamber and said head-piece connector of said head-piece includes male extension member, said female internal chamber designed to at least partially telescopically received in said male extension member of said head-piece and thereby connecting said head-piece to said head portion.

21. The bone implant system as defined in claim 20, wherein said male extension member includes at least one thread and said female internal chamber includes at least one corresponding thread.

22. The bone implant system as defined in claim 17, wherein said lower portion includes at least one thread.

23. The bone implant system as defined in claim 17, wherein said head-piece includes a mechanical mechanism, an electrical mechanism or combinations thereof.

24. The bone implant system as defined in claim 23, wherein said lower portion includes at least one interface designed to at least partially discharge an electrical current, a medical substance or combinations thereof.

25. The bone implant system as defined in claim 17, wherein said lower portion, head, head-piece or combinations thereof are at least partially include a coating material, said coating material including a compound that facilitates in the insertion, securing, or combinations thereof of the lower portion in said bone, cartilage, or combinations thereof; promotes, inhibits, or combinations thereof bone, other tissue growth, or combinations thereof; inhibits rejection of said bone implant; inhibits rejection of components connected to said bone implant, located adjacent to said bone implant, or combinations thereof; reduces infection; reduces inflammation; reduces pain; promotes healing of surrounding tissue; combats cancer, other diseases, or combinations thereof; combats biological abnormalities; functions as a location indicator; functions as a visual indicator; or combinations thereof.

26. The bone implant system as defined in claim 17, wherein said lower portion, head, head-piece or combinations thereof at least partially include at least one medical substance.

27. The bone implant system as defined in claim 26, wherein said medical substance includes at least one anti-thrombogenic agent, steroid, thioprotese inhibitor, antimicrobial, antibiotic, tissue plasma activator, monoclonal antibody, antifibrosis compound, hormone, growth factor, anti-mitotic agent, immunosuppressive agent, sense or antisense oligonucleotide, nucleic acid analogue, inhibitor of transcription factor activity, anti-neoplastic compound, chemotherapeutic compound, radioactive agent, growth factor, antiplatlet compound, antitabolite compound, anti-inflammatory compound, anticoagulent compound, antimitotic compound, antioxidant, antimetabolite compound, anti-migratory agent, anti-matrix compound, anti-vital compound, anti-proliferative, anti-fungal compound, anti-protozoal compound, human tissue, animal tissue, synthetic tissue, human cells, animal cells, synthetic cells, bone-stimulation matter, bone-growth matter, bone activating matter or combinations thereof.

28. The bone implant system as defined in claim 17, wherein said lower portion, head, head-piece or combinations thereof are at least partially biodegradable.

29. The bone implant system as defined in claim 17, wherein said upper portion including a connection tower with an exterior threaded shaft, a closed-rod connector, an open rod connector, a cross connector, a universal polyaxial connector, a spinal plate connector, a wire fixation device, or an artificial ligament "facet".

30. The bone implant system as defined in claim 17, wherein said head-piece connector of said head-piece is positioned below said upper portion of said head-piece.

31. The bone implant system as defined in claim 17, wherein said head-piece is a single piece head-piece.

32. The bone implant system as defined in claim 17, including a sleeve, said sleeve including an opening designed to receive at least a portion of said lower portion of said screw, nail or post.

33. A bone implant system to connect bone, cartilage, or combinations thereof to a support system comprising a set of head-pieces and a screw, nail or post, said screw, nail or post having a head and lower portion, said head portion of said screw, nail or post including a head connector, said set of head-pieces including a plurality of different head-pieces, each of said head-pieces in said set of head-pieces including an upper portion and a head-piece connector, said head-piece connector for each of said head-pieces having a similar configuration and designed to be secured to said head connector on said head portion of said screw, nail or post, at least one of said head-pieces at least partially connected below said upper portion of said head-piece, a plurality of said head-pieces in said set of head-pieces having a differently configured upper portion designed to connect to differing components of said support system, said head-piece connector of a plurality of said head-pieces is positioned below said upper portion of said head-pieces.

34. A bone implant system to connect bone, cartilage, or combinations thereof to a support system comprising a set of head-pieces and a screw, nail or post, said screw, nail or post having a head and lower portion, said head portion of said screw, nail or post including a head connector, said set of head-pieces including a plurality of different head-pieces, each of said head-pieces in said set of head-pieces including an upper portion and a head-piece connector, said head-piece connector for each of said head-pieces having a similar configuration and designed to be secured to said head connector on said head portion of said screw, nail or post, at least one of said head-pieces at least partially connected below said upper portion of said head-piece, a plurality of said head-pieces in said set of head-pieces having a differently configured upper portion designed to connect to differing components of said support system, at least one of said head-pieces is a single head-piece.

* * * * *